(12) United States Patent
Kimberly

(10) Patent No.: US 6,986,987 B1
(45) Date of Patent: Jan. 17, 2006

(54) GENETIC POLYMORPHISM IN THE RECEPTOR FOR IGA

(75) Inventor: Robert P. Kimberly, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/744,373

(22) PCT Filed: Jul. 23, 1999

(86) PCT No.: PCT/US99/16762

§ 371 (c)(1),
(2), (4) Date: May 16, 2001

(87) PCT Pub. No.: WO00/05403

PCT Pub. Date: Feb. 3, 2000

Related U.S. Application Data

(60) Provisional application No. 60/094,096, filed on Jul. 24, 1998.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.2; 536/23.5; 536/24.31; 536/24.33

(58) Field of Classification Search ............... 435/91.1, 435/91.2, 6; 536/23.1, 24.1
See application file for complete search history.

(56) References Cited

U.S. PATENT DOCUMENTS 5,856,104 A * 1/1999 Chee et al. ................... 435/6

FOREIGN PATENT DOCUMENTS

WO      WO 99/52942     * 10/1999

OTHER PUBLICATIONS

Carayannopoulos et al. J.Exp. Med. vol. 183 Apr. 1996 1579-1586.*
Morton et al. JBC vol. 270, No. 50 Dec., 1995. pp. 29781-29787.*
Wines et al. American Assoc. of Immunologists, 2001.*
Hacker et al. Gut 1997 40 :623-627.*
Pennisi et al. Science vol. 281, 1998 1787-1789.*
Morton et al. (Immungenetics 1996 43:246-247).*
Ahern et al.(The Scientists. vol. 9 #15, p. 20, Jul. 24, 1995).*
Morton et al. Immunogenetics (1996) 43:246-247.*
Wu, J. et al., A novel polymorphism of Fc. gamma.RIIIa (CD16) alters receptor function and predisposes to autoimmune disease. J. Clin. Invest. Sep. 1997, vol. 100, No. 5, pp. 1059-1070.
Patry, C. et al., Identification of Fc.alpha. receptor (CD89) isoforms generated by alternative splicing that are differentially expressed between blood monocytes and alveolar machrophages. J. Immunol. 1996, vol. 156, pp. 4442-4448.
deWit, T.P.M. et al., Structure of the gene for the human myeloid IgA Fc receptor (CD89), J. Immunol. 1995, vol. 155, pp. 1203-1209.
van Dijk, T.B. et al., Cloning and characterization of Fc alpha Rb a novel Fc alpha receptor (CD89), isoform expressed in eosinophils and neutrophils. Blood Dec. 1, 1996, vol. 88, No. 11, pp. 4229-4238.
Reterink, T.J.F. etal., Alternative splicing of IgA Fc receptor (CD89) transcripts Gene Feb. 1996, vol. 175, No. 1-2, pp. 279-280.

* cited by examiner

*Primary Examiner*—Jeffrey Fredman
*Assistant Examiner*—Sally Sakelaris
(74) *Attorney, Agent, or Firm*—Gifford, Krass, Groh, Sprinkle, Anderson & Citkowski, P.C.

(57) ABSTRACT

A method and a package for identifying single nucleotide polymorphisms in FcαRI is useful in identifying individual susceptibility to a disease. FcαRI is active as a cellular receptor of IgA. The susceptibility and severity of an IgA related disease is determined by genotyping or phenotyping an individual for FcαRI.

10 Claims, 5 Drawing Sheets

ENWHSHTALN KEASADVAEP SWSQQMCQPG LTFARTPSVC K

SEQUENCE LISTING

<160> NUMBER OF SEQ ID NOS: 4

<210> SEQ ID NO 1
<211> LENGTH: 39

```
<212> TYPE: DNA
<213> ORGANISM: Artificial Sequence
<220> FEATURE:
<223> OTHER INFORMATION: Primer

<400> SEQUENCE: 1
tgtaaaacga cggccagtag cacgatggac cccaaacag                              39

<210> SEQ ID NO 2
<211> LENGTH: 38
<212> TYPE: DNA
<213> ORGANISM: Artificial Sequence
<220> FEATURE:
<223> OTHER INFORMATION: Primer

<400> SEQUENCE: 2
caggaaacag ctatgaccgg tgttccccac tttggtgc                               38

<210> SEQ ID NO 3
<211> LENGTH: 38
<212> TYPE: DNA
<213> ORGANISM: Artificial Sequence
<220> FEATURE:
<223> OTHER INFORMATION: Primer

<400> SEQUENCE: 3
tgtaaaacga cggccagtag aatatttccc tcacgtgc                               38

<210> SEQ ID NO 4
<211> LENGTH: 39
<212> TYPE: DNA
<213> ORGANISM: Artificial Sequence
<220> FEATURE:
<223> OTHER INFORMATION: Primer

<400> SEQUENCE: 4
caggaaacag ctatgaccct ggctcctctc tgccttcac                              39
```

GENETIC POLYMORPHISM IN THE RECEPTOR FOR IGA

RELATED APPLICATION

This patent application is based on U.S. provisional application Ser. No. 60/094,096 filed Jul. 24, 1998, entitled "Genetic Polymorphism in the Receptor for IgA".

FIELD OF THE INVENTION

The present invention relates generally to compounds and methods for identifying polymorphism in a cellular receptor, and more particularly, to compounds and methods for identifying and typing single nucleotide polymorphisms that code for [gA receptors and applying these polymorphisms to delineation of disease susceptibility and severity.

BACKGROUND OF THE INVENTION

Immunoglobulins are responsible for responding to antigenic biochemicals encountered by a host eukaryotic organism. Immunoglobulin binding by a host receptor is important in activating immunological responses to an antigen. As a result, polymorphic receptor variations between individual hosts is expected to have implications in the relative susceptibility of individuals to similar antigenic challenge.

Recent advances in our understanding of the molecular structure and diversity of immunoglobulin receptors have focused attention on opportunities for insights into their role in the pathogenesis of antibody-mediated acute and chronic inflammation.

The IgG binding receptors have been extensively studied. These studies illustrate several aspects of receptor polymorphism that are important in understanding the utility of receptor genotyping individuals. Three distinct families of human receptors for the Fc domain of IgG (FcγRI, FcγRII, and FcγRIII) with different functional potential have been identified (1–3). Within these three FcγR families of related yet diverse molecules, distinct genes and alternative splice variants lead to series of receptor isoforms that have striking differences in the extracellular, transmembrane and intracellular regions. In addition, most receptor isoforms have structurally defined allelic polymorphisms (4–9). The various FcγR isoform; have different functional capacities based on different functional domains and/or sequence motifs. Furthermore, allelic variants of FcγRIIa, FcγRIIIa and FcγRIIIb also have distinct functional capacities (Preliminary Results; 4,9–13). For example, the alleles of FcγRIIa, which differ at amino acid position 131, differ substantially in their capacity to ligate human IgG2 (9,10,12,13) while the F/V-176 alleles of FcγRIIIa differ in their capacity to ligate human IgG1 and IgG3 (4).

Human neutrophils constitutively express FcγRIIa and FcγRIIIb, both of which have functionally significant allelic variants. FcγRIIa has an ITAM signaling motif in the cytoplasmic domain (14), mediates signaling events that are dependent on both phosphorylation and dephosphorylation, and interacts with actin filaments suggesting direct involvement in phagocytosis (15). Although the functional capacity of FcγRIIIb has been more controversial, in a myeloid environment FcγRIIIb initiates a range of cell programs (9,15–17). Importantly, the expression of FcγRIIIb is restricted to neutrophils (and eosinophils). FcγRI expression is inducible on neutrophils by IFNγ or IL-10 (18–20).

Human monocytes constitutively express FcγRIa and FcγRIIa; and with differentiation into monocyte-macrophages, they express FcγRIIIa and FcγRIIb. FcγIa and FcγRIIIa associate with FcεRI γ-chain which has an ITAM signaling motif, and both receptors can initiate degranulation, a respiratory burst and phagocytosis. FcγRIIb is distinct in having an inhibitory ITIM motif (21,22). Most carefully studied on B lymphocytes, FcγRIIb recruits phosphatases (SHP1 and SHIP) to its signaling complex and downregulates net signaling function (23–26).

In contrast to the Fcγ receptors, Fcα receptors are comprised of a single family of molecules most probably derived by alternative splicing from a single gene (27–32). The dominant protein product, FcαRIa (CD89), is a transmembrane protein which is heavily and variably glycosylated (33,34). Like FcγRIa and FcγRIIIa, FcαRIa lacks recognized signaling motifs in its cytoplasmic domain. It associates with FcεRI γ-chain which has an ITAM (35), but unlike FcγRIIIa, FcαRIa does not require the FcεRI γ-chain for expression. Similar to FcγRIa and FcγRIIIa, FcαRIa can initiate degranulation, a respiratory burst and phagocytosis at least in some experimental systems (36–38).

FcαRIa is constitutively expressed on human neutrophils and monocytes with about 6,000–7,000 copies per cell. Its expression is upregulated on activated neutrophils, including exudative neutrophils obtained from the gingival crevice and kidney glomeruli. Among cytokines, TNFα, IL-8 and GM-CSF increase surface expression of FcαRIa while IFNγ and TGFβ downregulate it (39). Alleles of FcαRIa are unexplored.

Immunoglobulin A (IgA) plays a prominent role in host defense at mucosal surfaces and in secretions such as tears, saliva and sweat where secretory IgA is the predominant immunoglobulin isotype. IgA appears to serve as a non-inflammatory regulator of the local immune response through the production of IL1ra and the absence of production of typical pro-inflammatory cytokines (40–44). These effects contrast with the well known anti-microbial defense functions of IgM and IgG which activate cell programs for inflammation and microbial destruction which may, in turn, injure surrounding host tissues. However, it is now recognized that receptors for IgA (FcαR) and for IgG (FcγR) depend upon tyrosine activation motifs for their function and that FcαRI (CD89), FcγRI (CD64) and FcγRIII (CD16a) use the identical FcεRI γ-chain for signaling. Consequently, the critical question of how these γ-chain associated receptors generate such divergent cell programs comes sharply into focus. Indeed, in the gingival lesion of chronic periodontal disease (PD) where both IgAs and IgGs are abundant, the balance of pro-inflammatory and anti-inflammatory programs is critical. Identification of the pivotal anti-inflammatory signaling elements differentially engaged by FcαRI provides a strategy for selective intervention and a target for therapeutic development. IgA through its prominent role in protecting surface tissues against invasion by pathogenic organisms is found throughout the respiratory, gastrointestinal and genitourinary tracts. The progression of diseases associated with these tracts is expected to relate to FcαR function.

Periodontal disease serves as a model for other diseases involving IgA activity. These other diseases include systemic lupus erythematosus (SLE), systemic vasculitis, and IgA nephropathy.

Periodontal disease is a chronic, recurrent inflammatory condition initiated and sustained by subgingival plaque bacteria but defined by the host immune system's inflammatory response which results in destruction of structures supporting the teeth (45–50). While bacterial pathogens and their products can damage host supporting tissues, disease can also arise from an exuberant inflammatory immune response by the host. Normally, this response is self-limited and the organism is eliminated. Some individuals, however, seem more susceptible to persistent or recurrent gingival disease, and this may relate to inherent differences in their immune system response. Indeed, some mechanisms of PD may resemble other chronic inflammatory conditions even though PD's distinctive features depend on the unique characteristics of the gingiva, teeth, supporting structures and microorganisms that reside in the oral cavity.

Among the organisms associated with PD, *Porphyromonas gingivalis* has been strongly implicated in adult PD (51,52). *P. gingivalis*-derived proteases damage tissue directly, as well as indirectly through the induction of collagenase secretion and interruption of complement-mediated defenses (53–56). Despite subtle differences in the chemical structure and biological properties of its lipopolysaccharide (LPS) relative to that from enterobacteria, *P. gingivalis* LPS induces mononuclear phagocytes to release inflammatory cytokines including TNFα, IL-1, and IL-6 (57–60). Fimbriae and other surface components of *P. gingivalis* also stimulate macrophages to produce IL-1 (61, 62). Of the two isoforms of IL-1, IL-1 is prominent in inflamed gingiva (63).

Secretion of IL-1ra by monocytes is a critical anti-inflammatory counterbalance (64). IL-1ra is an analog of IL-1 that blocks the effect of IL-1 by competitively binding to IL-1 receptors without transducing an activation signal. IL-1ra production is induced in monocytes and macrophages by multiple stimuli, IFNγ, IL-4, IL-6, IL-10 and bacterial LPS. IL-1ra production is also stimulated by IgG immune complexes through stimulation of FcγRIIa (CD32) and FcγRIIIa (CD16) (65–67), but the addition of LPS to FcγR stimulated cells augments IL-1β and suppresses IL-1ra production (68). IgA immune complex stimulation of FcαRI (CD89) leads to marked enhancement of IL-1ra production without IL-1 and TNFα (44). Since the ratio of IL-1ra:IL-1 has been implicated in adult periodontitis as well as several other inflammatory diseases including inflammatory bowel disease and systemic lupus erythematosus (69–71), the relative contributions of FcγR and FcαRI in stimulating local neutrophils and monocyte-macrophages is clearly of critical importance.

Recent association studies have suggested that Fcγ receptor polymorphisms (72–73) and that IL-1α/IL-1β genotype (74) may be related to the risk and/or severity of periodontal disease. These insights underscore the importance of the characteristics of the host immune response in defining risk for chronic inflammatory diseases, such as periodontal disease. Since various microorganisms play a role in the etiology of periodontal disease, it is also reasonable to expect that the susceptibility to disease, the severity and response to treatment or resistance would be associated with the MHC polymorphisms which are intimately involved in antigen processing and presenting antigens to T-cells (75). For example, several HLA-A and B alleles are associated with periodontitis among various racial and ethnic groups (76). The strongest association reported was with HLA-B35 (RR=6.03) in West Indies blacks. A similar association was observed between juvenile periodontitis and HLA-A33 and DR2 in African Americans under the age of 30 years (77). In a study of a Japanese family with early-onset periodontitis, high IgG titers were observed to *Porphyromonas gingivalis* and all subjects had HLA-DR52 and DQI in common (78–79). A study of renal transplant patients from Istanbul who received cyclosporine-A revealed that DR1 was significantly increased in those who did not develop gingival overgrowth compared to those who did (80). However, in Italian transplant patients who received cyclosporin and nifedipine the frequency of HLA-A19 was increased in those with gingival overgrowth compared to those without but did not reach statistical significance (81).

The literature also includes observations that genetic polymorphisms in several FcγR expressed on myeloid cells may influence the recurrence and severity of PD (82,83). These observations raise the possibility that similar polymorphisms in FcαRI may play an important role in the development of PD. FcαRI has several different splice isoforms (27–31) and is extensively, yet variably, glycosylated (33–34).

It would thus be desirable to provide an assay for determining the extent to which FcαRI is also genetically polymorphic, and whether single nucleotide polymorphisms (SNPs) lead to coding changes in both the extracellular and cytoplasmic domains. Characterization of the respective biologies of these SNPs is dependent on an understanding of the functional domains and molecular docking motifs of FcαRI.

It would also be desirable to assay genetically determined and post-translationally modified variations in FcαRI structure and to define the role of both extracellular and cytoplasmic domains essential for functions which may have significant impact on the progression of PD.

It would also be desirable to provide an assay to characterize the signaling elements associated with FcαRI and their role in determining unique FcαRI signaling events.

It would also be desirable to identify novel SNPs affecting FcαRI structure and function.

It would also be desirable to identify both pre- and post-translational variations and modifications of FcαRI and their impact on FcαRI function.

It would also be desirable to establish the role of FcαRI splice variants and of both FcαRI and FcαR polymorphisms in determining the ability of a host to fight certain bacterial and viral infections, the susceptibility to and/or severity of autoimmune diseases, as a prognosis indicator or to identify suitable vaccinations or treatments.

SUMMARY OF THE INVENTION

The present invention is a system and method for correlating the ability of a cell to bind immunoglobulin (IgA) and cellular susceptibility to a disease by identifying a FcαRI genotype of a cell and quantifying IgA binding by the cell expressing the FcαRI genotype. Thereafter, the IgA binding by the cell and IgA binding by a second cell expressing a second FcαRI genotype is compared.

The present invention uses a single nucleotide polymorphism or combinations thereof within a FcαRI genotype to identify individual susceptibility to a disease.

The methods of the present invention also extend to correlating the ability of a cell to bind IgA and cellular susceptibility to a disease through identifying a FcαRI phenotype of a given cell and quantifying IgA binding by said cell. Thereafter, IgA binding by the cell is compared to a second cell having a second phenotype of FcαRI. In particular, single nucleotide polymorphisms are responsible for genotypical and phenotypical differences in FcαRI herein.

The present invention further includes a commercial packaging including reagents for identifying single nucleotide polymorphisms in the FcαRI genotype or phenotype of an individual as a test to identify individual susceptibility to a disease. The reagents further include instructions for the use thereof.

DETAILED DESCRIPTION OF THE INVENTION

Figure 1:
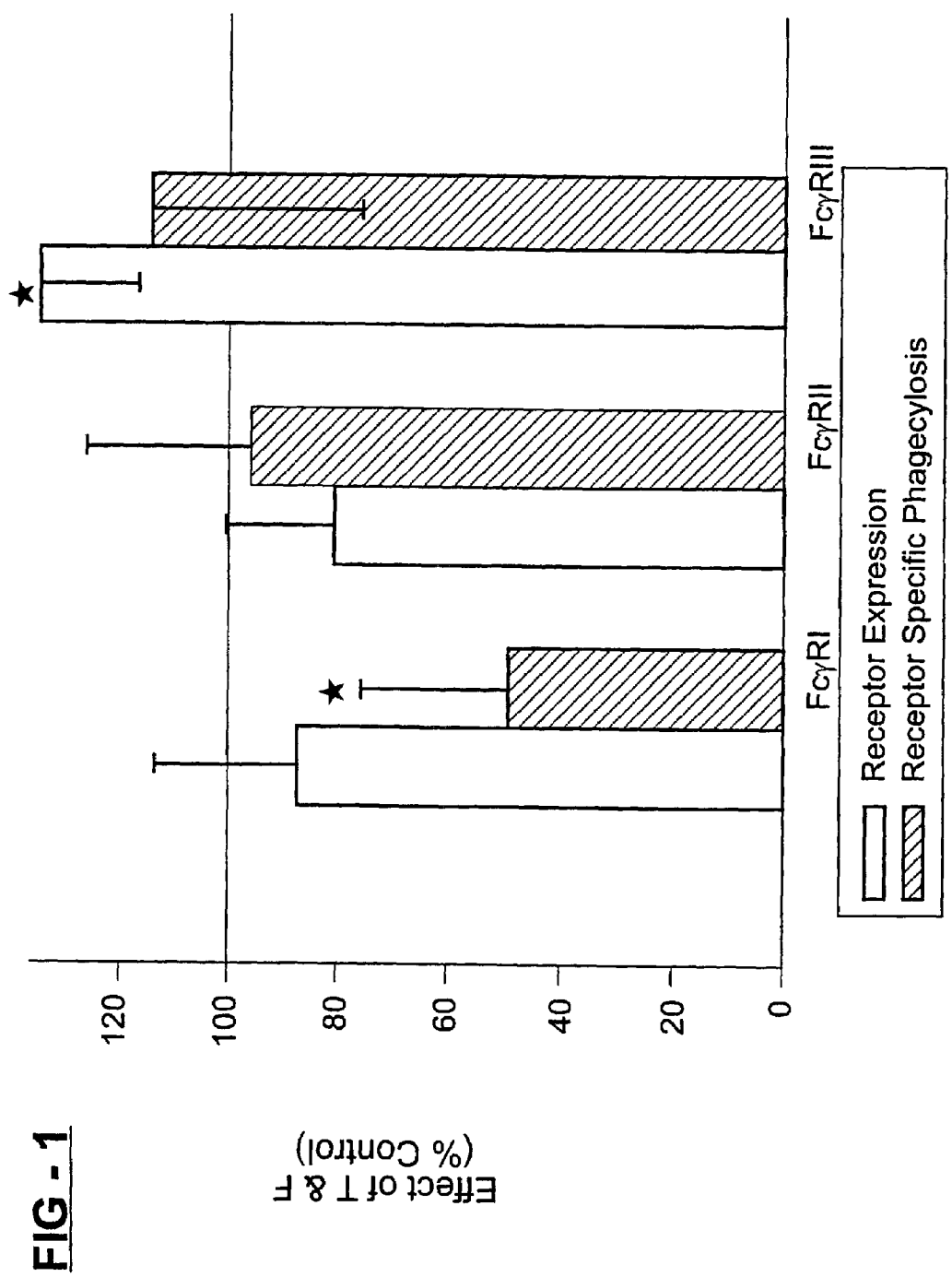
FIG. 1—TGFβ causes a significant (p<0.01) decrease in FcγRI specific phagocytosis in 18-hr cultured human monocytes. Phagocytosis by FcγRII and FcγRIII are unaffected by TGFβ but there is a modest increase in FcγRIIIa expression. Data are reported relative to untreated cells. Phagocytosis normalized to expression is 0.5, 1.2 and 0.9 for FcγRI, FcγRII and FcγRIII respectively.

The present invention provides methods for determining the allelic pattern for FcαRI genes in human patients. The methods encompass the use of allele specific oligonucleotides as hybridization probes and/or as primers for DNA amplification, as well as the use of direct DNA sequencing. Identification of receptor alleles may also be achieved immunologically, by contacting mucosal cells that express FcαRI receptors on their cell surface with antibodies that distinguish between different polymorphic forms of the receptor.

The present invention is based on the finding that allelic polymorphism in a gene encoding FcαRI receptor isoform results in functionally distinct gene products. The expression of a polymorphic receptor in an individual may have important consequences for the physiological activity of the receptor and thus for the functioning of the cell types that carry the receptor. Because of the important immunological role of IgA in mucosal immunity, the present invention has utility as a diagnostic to identify high risk patients that warrant early and aggressive treatment. As a diagnostic for infectious disease, the present invention has utility in predicting neonatal sepsis and thereby guiding the use of therapeutic gamma globulin. As a diagnostic for autoimmune disease, the present invention has utility in diseases illustratively including systemic lupus erythematosus, systemic vasculitis, IgA nephropathy, rheumatoid arthritis, systemic sclerosis, dermatomyositis, Hashimoto's thyroiditis, inflammatory bowel disease and Sjogren's syndrome. For cancer, the present invention has utility as an immune surveillance test for monitoring protective and nonprotective antibody levels in response to cancer therapies.

The present invention provides a method for identifying the FcαRI allelic pattern in human patients which comprises testing mucosal tissue cells or DNA from individual patients for the presence of different FcαRI allelic variants, using antibody based and/or nucleic based methods which are described in more detail below. The identification of receptor allelic patterns of the present invention further finds utility in identifying gene therapy as a means for providing more effective receptor alleles to a patient.

The present invention also encompasses the identification analysis of new allelic forms of FcαRI genes, the analysis achieved using methods well known in the art, such as for example, DNA sequencing; single strand conformational polymorphism analysis (SSCP) (84); "HOT" cleavage (85); denaturing gradient gel electrophoresis (DVGE) (86) and combinations thereof. Once a new polymorphism has been identified, immunological and/or molecular biological tests are used to genotype patients for the presence or absence of the polymorphism. For example, monoclonal antibodies specific to the protein encoding for a newly identified allele are prepared by well known methods; these antibodies can be used for genotyping the patient populations as described above. Alternatively, allele specific oligonucleotides are designed for use as probes and/or as primers in hybridization or PCR-based detection methods, respectively.

The present invention characterizes the signaling elements associated with FcαRI and their role in determining unique FcαRI signaling events. Using the yeast two-hybrid system with CD89 alpha chain cytoplasmic domain (CY) as "bait," novel molecular associations with the CY, the residues meeting these associations, and the potential dependence on serine/threonine phosphorylation are determined. Alternatively, the properties of CD89 alpha chain signaling alone, the regulation of γ-chain pairing with CD89 alpha chain, and the signaling elements engaged by CD89, as opposed to CD16 and CD64, are defined. A further method of characterizing the signal elements associated with FcαRI includes using stably transfected constructions with specific deletions, truncations and point mutations of CD89. The effect of these constructs on associations, the role of these interactions in modulating signaling and initiation of cell programs is thereby determined.

The present invention also encompasses identification of novel single nucleotide polymorphisms (SNPs) affecting FcαRI structure and function. SNPs are identified using direct cycle sequencing optimized for heterozygote detection, genomic DNA and cDNA obtained by RT-PCR from mRNA so as to provide a template to identify novel SNPs in normal donors, in PD, rheumatoid arthritis patients and in other patients suffering from diseases illustratively including connective tissue, autoimmune, bacterial and viral infection, and cancer. Through the establishment of statistically significant correlations between the different allelic forms of FcαRI (and allelic patterns formed by combinations of different alleles) and various physiological and/or clinical manifestations of variable FcαRI function, the role of naturally occurring point mutations in modulating signaling and initiation of cell programs is identified in homozygous genotype donors and in stable transfectants. These correlations are utilized to provide the diagnostic utilities of the present invention. In practicing the present invention, preferably the correlations sought are those between particular FcαRI allelic polymorphs and, for example: the risk for developing the aforementioned diseases; the effectiveness of antibodies protective against biologic- or tumor neo-antigens; and the risk of immune complex disease. In order to establish the impact of both pre- and post-translational variations and modifications of FcαRI on FcαRI function, the variation and expression of FcαRI splice variants is determined in circulating and in crevicular fluid myeloid cells from patients suffering from an aforementioned disease in relation to a disease free control group. An RT-PCR method is used to identify translational variations and modifications of the receptor. Preferably, the FcαRI "b" form is investigated for correlations through the use of different TM/CY. Gel electrophoresis of immunoprecipitated FcαRI from cell lines and ex vivo myeloid cells is used to identify different receptor molecular weights, as previously done with FcγRIIIa (17). Gel electrophoresis serves to characterize the glycosylation state in relationship to the ligand binding ability of the receptor polymorph. Translational variations and modifications of receptor glycosylation in patients suffering from an IgA related immune response disease can be correlated with SNPs of the receptor, as well as with the glycosylation status of both IgA and IgG.

Statistical methods, illustratively including a 2×3 chi-square test is used to determine allele frequencies in disease and control groups. In this manner, it is possible to obtain statistically significant correlations between a given disease and FcαRI alleles and thereby a diagnostic as to disease susceptibility and clinical outcome.

In practicing the present invention, the FcαRI allelic pattern in an individual patient is determined by either: 1) immunological detection of one or more allelic forms of FcαRI polypeptides present on the surface of appropriate immune cells ("phenotypic characterization"); or 2) molecular detection of the DNA or RNA encoding one or more FcαRI allelic forms using nucleic acid probes, with or without nucleic acid amplification or sequencing ("genotypic characterization").

In one method, myeloid cells, mucosal cells, or those of any tissue expressing CD89 or subsets thereof are isolated from a patient to be tested using methods that are well known in the art, such as, for example, gradient centrifugation and/or immunoadsorption. Antibodies that are capable of distinguishing between different allelic forms of FcαRI are then applied to the isolated cells to determine the presence and relative amount of each allelic form. The antibodies may be polyclonal or monoclonal, preferably monoclonal. Measurement of specific antibody binding to cells may be accomplished by any known method, including without limitation quantitative flow cytometry, or enzyme-linked or fluorescence-linked immunoassay. The presence or absence of a particular allele, as well as the allelic pattern (i.e. homozygosity vs. heterozygosity) is determined by comparing the values obtained from the patient with norms established from populations of patients of known genotypes.

In an alternate embodiment, DNA is obtained from a patient, and the presence of DNA sequences corresponding to particular Fcα receptor alleles is determined. The DNA may be obtained from any cell source or body fluid. Non-limiting examples of cell sources available in clinical practice include blood cells, buccal cells, cervicovaginal cells, epithelial cells from urine, fetal cells, or any cells present in tissue obtained by biopsy. Body fluids include blood, urine, cerebrospinal fluid, and tissue exudates at the site of infection or inflammation. DNA is extracted from the cell source or body fluid using any of the numerous methods that are standard in the art. It is understood that the particular method used to extract DNA will depend on the nature of the source.

Once extracted, the DNA may be employed in the present invention without further manipulation. Alternatively, the DNA region corresponding to all or part of the FcαRI may be amplified by PCR or other amplification methods known in the art. In this case, the amplified regions are specified by the choice of particular flanking sequences for use as primers. Amplification at this step provides the advantage of increasing the concentration of FcαRI DNA sequences. The length of DNA sequence that can be amplified ranges from 80 bp to up to 30 kbp. Preferably, primers are used that define a relatively short segment containing sequences that differ between different allelic forms of the receptor.

The presence of Fcα receptor allele-specific DNA sequences may be determined by any known method, including without limitation direct DNA sequencing, hybridization with allele-specific oligonucleotides, and single-stranded conformational polymorphism (SSCP). Direct sequencing may be accomplished by chemical sequencing, using the Maxam-Gilbert method (87), or by enzymatic sequencing, using the Sanger method (88). In the latter case, specific oligonucleotides are synthesized using standard methods and used as primers for the dideoxynucleotide sequencing reaction.

Preferably, DNA from a patient is subjected to amplification by polymerase chain reaction (PCR) using specific amplification primers, followed by hybridization with allele-specific oligonucleotides. Alternatively, SSCP analysis of the amplified DNA regions may be used to determine the allelic pattern. Most preferably, allele-specific PCR is used, in which allele-specific oligonucleotides are used as primers and the presence or absence of an amplification product indicates the presence or absence of a particular allele.

In an alternate embodiment, cells expressing FcαRI are isolated by immunoadsorption, and RNA is isolated from the immunopurified cells using well-known methods such as guanidium thiocyanate-phenol-chloroform extraction (89). The isolated RNA is then subjected to coupled reverse transcription and amplification by polymerase chain reaction (RT-PCR), using allele-specific oligonucleotide primers. Conditions for primer annealing are chosen to ensure specific reverse transcription and amplification; thus, the appearance of an amplification product is diagnostic of the presence of the allele specified by the particular primer employed. In another embodiment, RNA encoding FcαRI is reverse-transcribed and amplified in an allele-independent manner, after which the amplified Fcγ receptor-encoding cDNA is identifiable by hybridization to allele-specific oligonucleotides or by direct DNA sequencing.

The term "allelic form" is intended to mean an alternative version of a gene encoding the same functional protein but containing differences in nucleotide sequence relative to another version of the same gene.

The term "allelic polymorphism" or "allelic variant" is intended to mean a variation in the nucleotide sequence within a gene, wherein different individuals in a general population express different variants of the gene.

The term "predetermined polymorphic DNA sequence" is intended to mean a known allelic variant.

The term "allelic pattern" is intended to mean the identity of each of the two copies of a particular gene in a patient i.e., homozygosity or heterozygosity.

The term "allelic pattern" is used herein interchangeably with "genotype."

The term "genotyping" as used herein as being the process of determining the allelic patterns of a human individual.

The term "point mutation" as used herein is intended to mean a mutation involving a single nucleotide.

The term "silent mutation" as used herein is intended to mean a change of a nucleotide within a gene sequence that does not result in change in the coded amino acid sequence.

The term "missense mutation" as used herein is intended to mean a change of a nucleotide within a gene sequence that results in a change in the meaning of a codon, thereby changing the coded amino acid.

The term "frame shift mutation" as used herein is intended to mean a mutation involving the insertion or deletion of a single nucleotide that results in the remaining downstream sequence being transcribed or translated out of phase.

The term "amplificafion" in regard to DNA is intended to mean the use of polymerase chain reaction (PCR) to increase the concentration of a particular DNA sequence within a mixture of DNA sequences (90).

The term "chemical sequencing" in regard to DNA is intended to mean a method in which DNA is randomly cleaved using individual base specific reactions, illustratively including Maxam-Gilbert sequencing.

The term "enzymatic sequencing" in regard to DNA is intended to mean a method in which single stranded DNA is copied and randomly terminated using DNA polymerase, illustratively including the method of Sanger (88).

The term "effective FcαRI mediated immune response" is intended to mean immune response that results in the lessening of at least one symptom of a disease to which the host immune response is directed.

While the description of the present invention that follows is largely directed to periodontal disease, it is appreciated that the receptor mediated immune response is similar in that of other human diseases of tissues protected by neutrophils and monocytes. The diseases illustratively including systemic lupus erythematosus, systemic vasculitis, IgA nephropathy, rheumatoid arthritis, systemic sclerosis, dermatomyositis, Hashimoto's thyroiditis, inflammatory bowel disease and Sjogren's syndrome.

The insights into the structure and critical function of FcRs (91–93) and into the genetics of FcγRs in periodontal disease (82,83), coupled with an appreciation of the capacity of phagocytes to release cytokines and other inflammatory mediators, suggest that FcR-mediated triggering of neutrophils and Mϕ is a central convergence point in PD. From this perspective, FcγR initiate synthesis and secretion of pro-inflammatory cytokines, release of degradative enzymes and release of reactive oxygen intermediates capable of tissue damage (94–96). As counterpoint, IgA immune complex stimulation of FcαRI (CD89) leads to marked enhancement of IL-1ra production without IL-1 and TNFα (44).

Role of the cytoplasmic domain of the ligand binding α-chain in modulating receptor function. Co-transfection and co-immunoprecipitation studies indicate that FcαRI (CD89), FcγRIa (CD64) and FcγRIIIa (CD16a) associate with FcϵRI γ-chain (2,86). FcϵRI γ-chain contains an immunoreceptor tyrosine activation motif (ITAM), is actively tyrosine- and serine/threonine-phosphorylated, and plays a critical role in function (2,14,98,99). Extrapolating from receptor chimera data and from experiments with point mutagenesis of receptor associated ITAMs, many investigators have concluded that FcϵRI γ-chain is both necessary and sufficient for signal transduction (3,100). Indeed, within the field of Fc receptors, there is the common presumption that FcϵRI γ-chain is the exclusive signaling pathway for those receptors which associate with it.

However, other evidence suggests that FcϵRI γ-chain is not the sole actor in FcϵRI γ-chain-associated Fc receptors. In 1993, Hogarth and colleagues demonstrated that the cytoplasmic domain (CY) of murine FcγRI ligand binding chain (CD64; α-chain) is actively phosphorylated after treatment of J774 cells with phorbol myristate acetate (101). Transfection studies suggest that FcγRI, expressed without γ-chain, appears to be able to mediate some functions like endocytosis (102–104). The present invention demonstrates that the α-chain CY, despite the absence of recognized signaling motifs, participates in initiating cell programs. The FcγRI α-chain CY does interact with actin binding protein (105) and a naturally occurring FcγRI α-chain tail-minus mutant in the NOD mouse has some functional differences (106). While human blood monocytes incubated for 18 hrs with rIFNα show a modest increase in both FcγRI-specific and FcγRIII-specific phagocytosis, TGFβ causes a significant decrease in FcγRI mediated phagocytosis yet no effect on FcγRIII (FIG. 1).

Figure 2A:
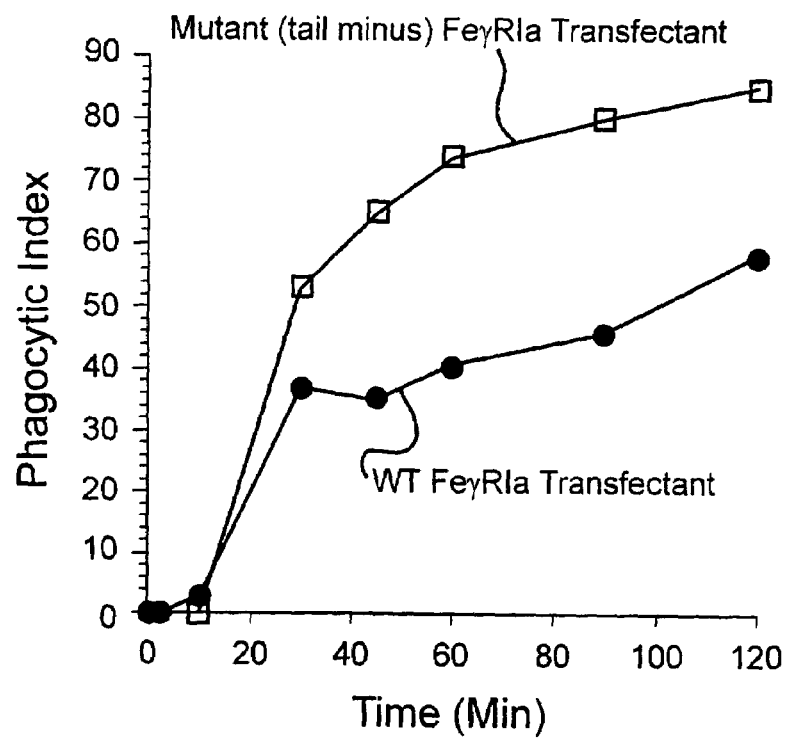
FIG. 2A—Receptor specific phagocytosis (E-22.2 F(ab)'$_2$) by transfected human wild type and mutant tail minus FcγRIa in P388D1 cells.
Figure 2B:
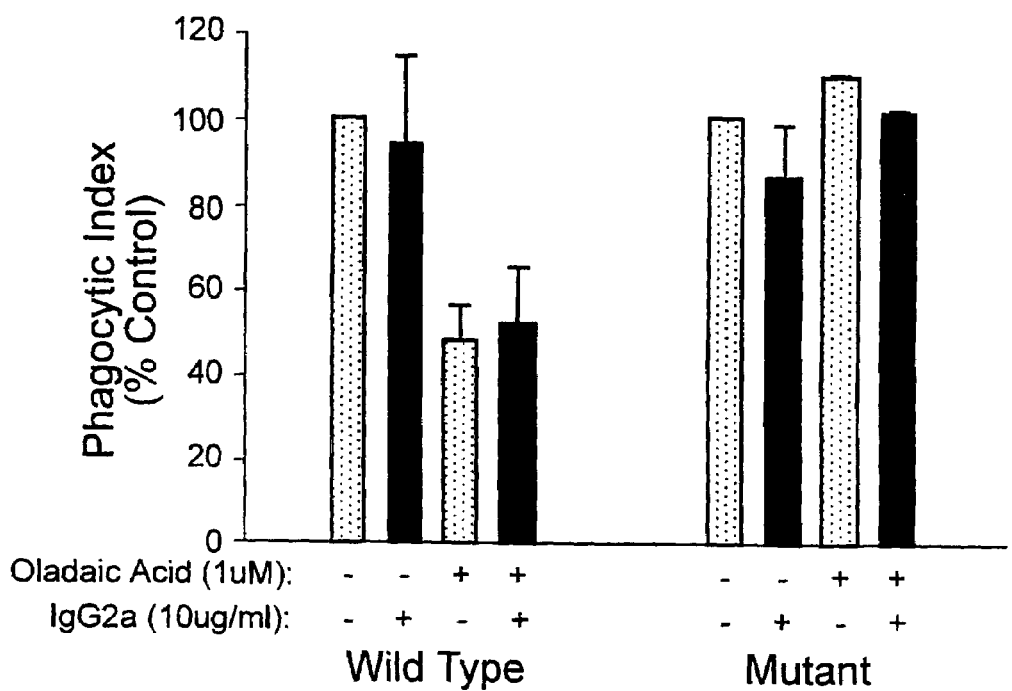
FIG. 2B—Pre-incubation of transfected P388D1 cells with saturating levels of murine IgG2a and/or okadaic acid before addition of E-22.2 did not significantly alter FcγRIa phagocytosis. Binding of the E-22.2 is not affected by either pre-incubation.
Figure 3:
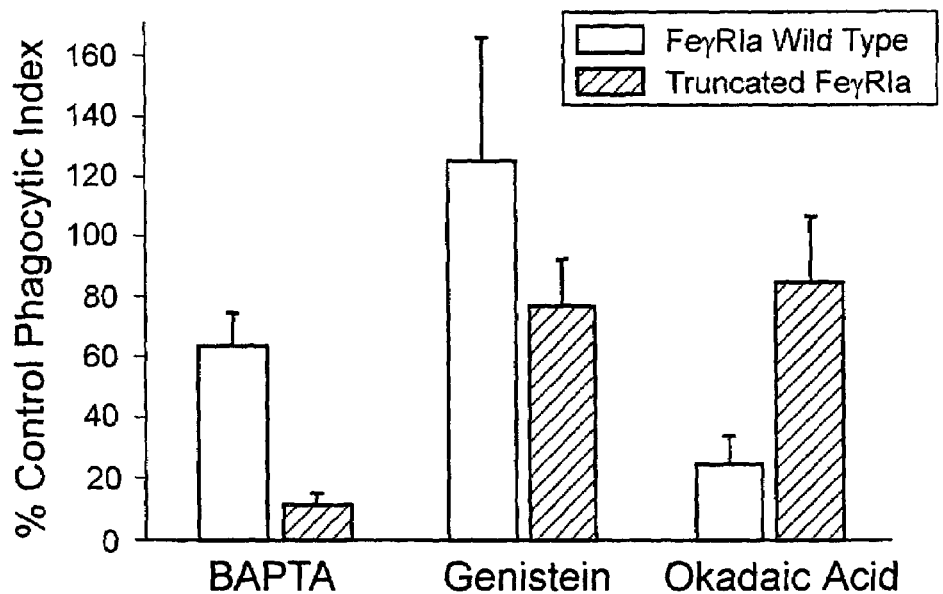
FIG. 3—Differential affects of the calcium chelator BAPTA, the protein tyrosine kinase inhibitor genistein and the ser/thr phosphatase inhibitor okadaic acid on receptor specific phagocytosis mediated by transfected WT and MT FcγRI. Data are presented relative to control untreated cells.
Figure 4:
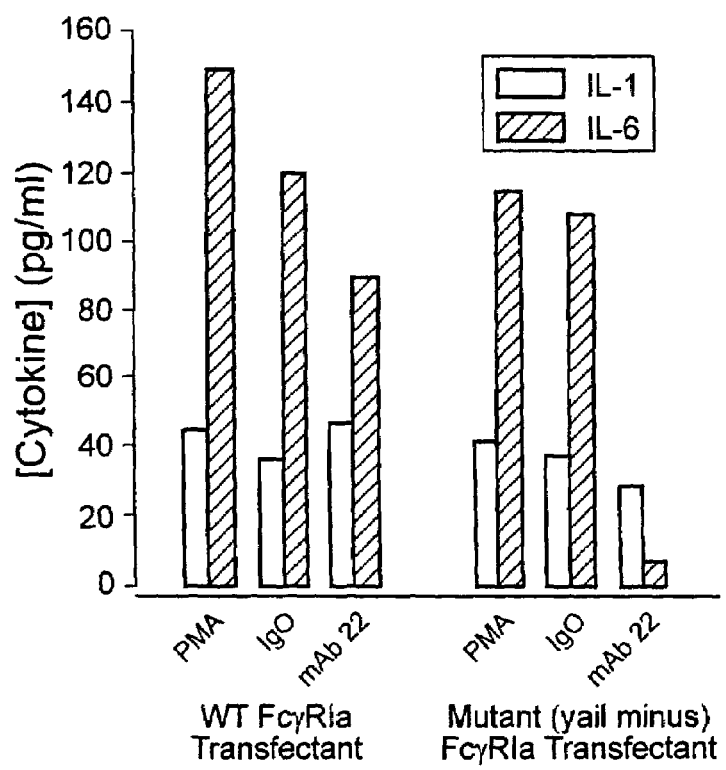
FIG. 4—Cross-linking of transfected WT FcγRIa with receptor-specific mAb 22 induces production of both IL-1β and IL-6 while MT FcγRI only induces IL-1β. Data are presented as pg/ml above control unstimulated cells after 8 hours.

Contribution of α-chain CY to FcγRI function. P388D1 cells stably transfected with human wild-type (WT) and human CY-minus (MT) FcγRI are studied. Both cells lines express comparable levels of receptor. Like the truncated receptor in the NOD mouse, albeit more subtly, the MT in P388D1 endocytoses more slowly than WT. The MT phagocytoses less (FIG. 2A), an effect which is independent of engagement of the ligand binding site (FIG. 2B); it shows a greater sensitivity to chelation of $[Ca^{2+}]_i$ and to the PTK inhibitor genistein and is resistant to the effects of okadaic acid (FIG. 3), suggesting a differential engagement of signaling elements compared to WT. Furthermore, while both WT and MT synthesize IL1β, MT is markedly deficient in IL6 production at 8 hrs (FIG. 4).

A model is suggested by the recognition that cytoplasmic domains of different associated chains can interact and modulate function (14,107,108). For example, in the FcϵRI complex which is comprised of one α, one β and one γ homodimer, both the src family tyrosine kinase Lyn and the PKC isoform delta are constitutively associated with β which in turn facilitates tyrosine phosphorylation and threonine phosphorylation on γ, respectively (98,109,110). Although the FcγRIa complex does not have a corresponding β chain, the CY of the α-chain is involved in the interaction between the α-chain and may serve to recruit (or perhaps impede) signaling element(s); the okadaic acid data suggests that this element(s) may at least involve ser/thr phosphorylation. Of course, since the primary sequence of the α-chain CY domains for FcγRI, FcγRIII, and FcαRIa are different (Table 1), the contributions of each CY domain may provide the basis for the unique receptor function.

Inspection of the FcγRIII CY domain suggests several potential ser/thr phosphorylation sites (PKC motif: SSTRD and casein kinase 2: SSTRDW) and the present invention shows data parallel to that on FcγRIa, demonstrating that the CY domain is actively phosphorylated in vitro. The observation by Geisler and colleagues (111) that truncation FcγRIIIa CY alters the ability of the receptor to induce calcium flux further supports a role for the CY, and suggesting that Eibl's data (44) showing FcαRI stimulates primarily IL1ra and not TNFα production can be explained by a unique CY mechanism of the present invention.

To explore the mechanism and role of the CY by identifying intracellular interactions between proteins, the yeast two-hybrid system is used in the present invention with the GAL4 transcriptional activator, with the CY domain as "bait" cloned in-frame into the pGBT9 vector containing the DNA binding domain of the GAL4 transcriptional activator and with three distinct cDNA libraries cloned into pACT with the GAL4 activation domain. As human cDNA libraries, an EBV-transformed PBMC library, a PHA-stimulated PBMC library and an unstimulated PBMC library have been used. Recognizing that achieving the native conformation of the CY domain is the goal in the two hybrid system, three different binding domain constructs: (1) binding domain—CY, (2) binding domain—6 glycines-CY, and (3) binding domain—6gly-CY-6gly-CY have been constructed. With this approach, a novel member of the band 4.1 family which associates with FcγRI CY but not with FcγRIII CY, CR1 CY and several other control baits has been identified.

Figure 5:
FIG. 5—Sequence of the cytoplasmic domain of FcαRI (CD89) showing potential kinase phosphorylation sites.

Examination of FcαRIa CY sequence reveals that it is quite distinct from the other FcεRI γ-chain associated receptors (Table I) and that it contains several potential serine phosphorylation sites (FIG. 5). In the two hybrid system, the present invention uses the native CY (with or without the 6 glycine linker), the CY with S to D/E to "mimic" serine phosphorylation, and then a variety of truncations and point mutations to establish the role of docking regions and sites with phosphorylation motifs.

Figure 6:
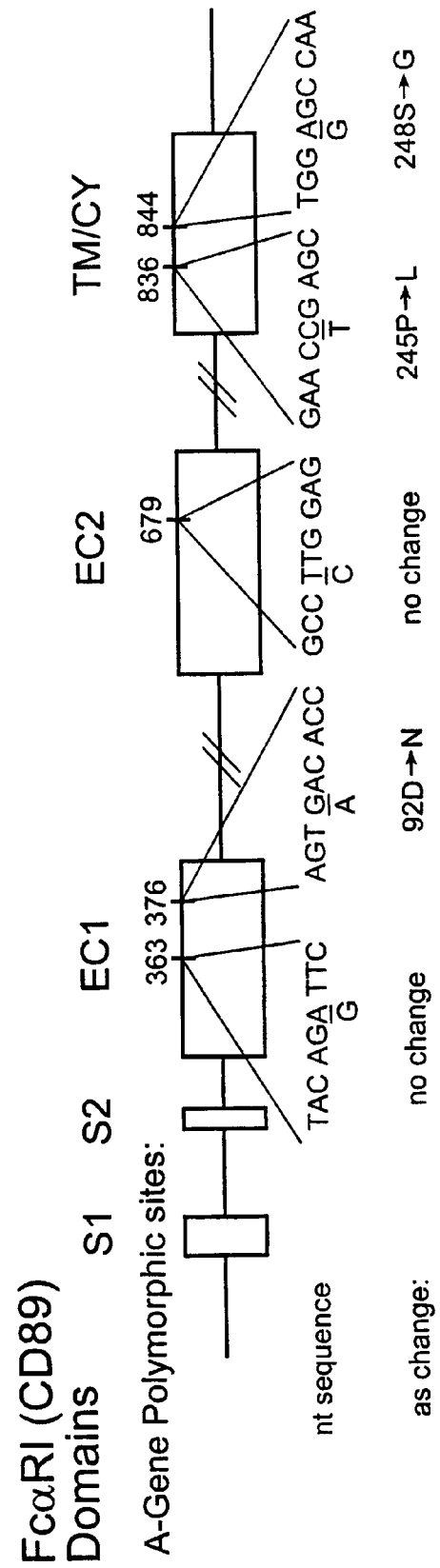
FIG. 6—Genomic organization of FcαRI (CD89) showing polymorphic sites.

Based on the precedent of biologically important SNPs in the coding regions of FcγRIIA, FcγRIIIA and FcγRIIIB, on the recognition of the influence of the FcγRIIA and FcγRIIIB polymorphisms on the risk for PD, and on the knowledge that PD lesions are rich in both IgG and IgA, the present invention identifies novel SNPs in FcαRIA. Morton and colleagues have reported a silent SNP in codon 87 (AGA→AGG, remains Arg), an Asp→Asn in codon 92 (GAC→AAC) of extracellular domain 1 (EC1) and a Phe→Leu at codon 132 (TTT→CTT) of EC2 (112). Using direct cycle sequencing of cDNA derived from mRNA, FcαRIA of 39 normals and 31 patients with rheumatoid arthritis (RA) were examined. However, of much greater interest are two novel polymorphisms of the present invention in the CY domain,—a Pro→Leu at residue 245 and a Ser-Gly at residue 248 (FIG. 6). The Pro→Leu is very uncommon with a gene frequency in our population suggesting that it will be classified as a mutation. The Ser→Gly polymorphism has gene frequencies of 0.874 and 0.126 respectively with no difference between normals and RA patients. Inspection of the full sequence of the FcαRIa CY indicates that both the Pro and the Ser are part of a putative casein kinase I phosphorylation site (FIG. 6). Thus, the present invention shows that there are FcR polymorphisms which directly affect signal transduction rather than ligand binding as the mechanism for altered function.

Gamma (γ) chain plays a critical role in the function of FcγRIa, FcγRIIIa and FcαRI (2). Through physical association in the plasma membrane with the ligand-binding alpha chain of these receptors, γ-chain provides a necessary signaling element(s) including an ITAM (immunoregulatory tyrosine-based activation motif) (14). The role of the phosphorylated tyrosine residues (pY) is to increase the binding affinity for SH2-containing molecules, but sequence analysis of the γ-chain cytoplasmic domain reveals multiple serine and threonine residues in/near the ITAM. Since the thr residues are in the ITAM [γ-chain CY: RLKIQVRKAAITSYEKSDGVYTGLSTRNQETYETLKHEKPPQ] which predicts direct contact with SH2-containing molecules attempting to "dock," one might imagine these residues as important modulators of this process.

FcαRIa is known to be differentially glycosylated in different cell types (33,34) and it has been shown that an altered glycosylation pattern of receptor in certain diseases such as IgA nephropathy. Work with FcγRIIIa expressed on NK cells and on monocytes-macrophages provides a framework which suggests that these glycosylation differences in FcαRIa are important. FcγRIIIa expressed on NK cells and on monocyte-macrophages is also differentially glycosylated despite identical protein cores and these different glycoforms have different affinities for ligand. The macrophage form has a lower apparent Mr, is lower in sialic acid content, and has a lower affinity for IgG (113). The broad range of apparent Mr which is greater than can be explained by known splice isoforms of FcαRI is consistent with disease-associated changes in glycosylation altering receptor function.

Figure 8:
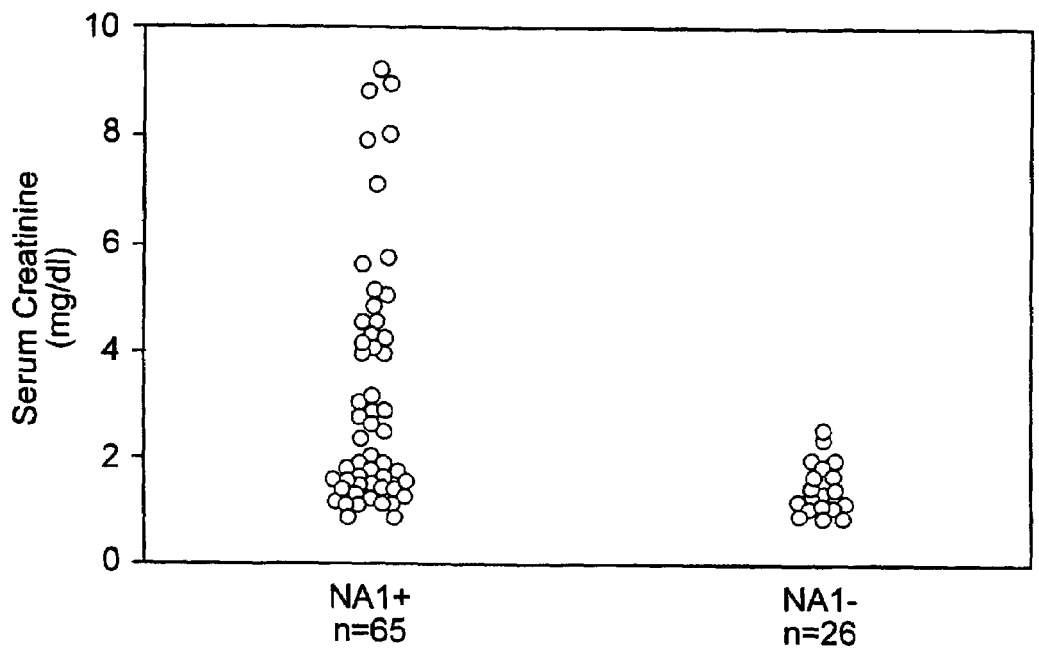
FIG. 8—Serum creatinine values from patients with Wegener's Granulomatosis with renal disease.

Several lines of evidence suggest that Fc receptor polymorphisms are important in the development of disease phenotype in chronic inflammatory diseases. The present invention shows that alleles for both FcγRIIa and FcγRIIIa are altered in their representation in SLE with low binding alleles associated with the SLE phenotype and high binding alleles (176V) protecting against glomerulonephritis (4,114). It is also shown that alleles of FcγRIIIB predict the severity of glomerulonephritis in ANCA-positive vasculitis such as Wegener's Granulomatosis (FIG. 8). The data presented herein shows that the novel Ser→Gly in the CK1 site of the FcαRI CY domain is markedly enriched in chronic inflammatory disease (SLE).

Fc receptor polymorphisms are also important in host defense against infectious disease (115–117). FcγRIIa, FcγRIIIa, FcγRIIIb and FcαRIa are expressed on neutrophils and mononuclear phagocytes, and myeloid cells essential for host defense. Since FcγRIIa-R131 binds human IgG2 poorly and IgG2 is a component of the host immune response to encapsulated bacteria, individuals homozygous for FcγRIIa-R131 may be at greater risk for bacterial infection. Similarly, individuals homozygous for the low activity FcγRIIIb-NA2 may be at greater risk for infection (118). Two initial reports (82,83) of associations of FcγRIIa and FcγRIIIb polymorphisms with PD phenotype (susceptibility, severity, recurrence) suggest that FcγR-related function may be important in the pathogenesis of PD. However, while these reports in PD are suggestive, neither has considered the role of the novel FcαRIa polymorphisms described above. Taken together, this repertoire of genetic variants provides a tool to anticipate phenotype, especially with regard to severity of disease.

The present invention characterizes the signaling elements associated with FcαRI and their role in determining unique FcαRI signaling events. Current evidence has been interpreted as demonstrating that the γ-chain ITAM is both necessary and sufficient for the function of the FcεRIγ-chain associated Fcγ receptors (CD16 and CD64). However, the present invention shows that the cytoplasmic domains of the ligand binding α-chains in these γ-chain receptor complexes are functionally important and provide the basis for diversity in signaling among these FcεRIγ-chain associated receptors. The Fc receptor for IgA also forms a receptor complex with the γ-chain, and there is clear precedent that this Fcα receptor complex is functionally distinct from the Fcγ receptor complexes. Accordingly, the present invention shows that the cytoplasmic domain (CY) of the ligand binding α-chain of CD89 can modulate the functional responses of the receptor complex and/or possibly elicit functional responses independently of the γ-chain.

Functional impact of FcεRIγ-chain pairing with FcαRI α-chain. FcαRI has some homology with FcγR encoded on human chromosome 1 and with the KIR family of receptors found proximate to FcαRI on human chromosome 19 (119). Members of the KIR protein family are not known to associate with γ-chain. To determine the functional properties of FcαRI expressed as a protein associated or not associated with FcεRIγ-chain. For these studies, transfection uses wild type FcαRI and a mutant form of FcαRI that does not associate with γ-chain into an appropriate cell line. Previous studies in a double transfection system using the γ-chain lacking B cell line IIA1.6 has shown that Arg209 in the TM domain of FcαRI is required for association with the γ-chain (35). Confirmation of association or non-association of γ-chain in FcαRI immunoprecipitates from digitonin lysates of transfected cells utilizes a polyclonal anti-γ-chain Ab.

The choice of cell line for these studies is crucial because the cell line must be capable of performing appropriate functions when stimulated, and possess the necessary intracellular constituents to interact with FcαRI. For example, engagement of FcαRI is known to activate the src-family tyrosine kinase lyn (120,121), to activate the tyrosine kinase syk (120,121), to induce secretion of IL-1ra and to inhibit LPS induced secretion of IL-β (and TNFα)(44). Suitable cell lines illustratively include: the murine monocyte-macrophage-like cell lines J774, P388D1 and myeloid cells capable of eliciting appropriate functional responses. Suitable cell lines such as these are transfectable with plasmids and can express transfected human gene products (2,122,123); endogenously express the γ-chain (2). P388D1 has been used extensively to analyze the structural requirements for initiation of functional responses by human Fcγ receptors (especially FcγRIa and FcγRIIa) and is the preferred choice of host cell for FcαRI transfections.

Activation of both early signaling events and cell programs are examined in stably transfected lines expressing the wild type and mutant non-γ-chain associated forms of FcαRI. Early signals include the phosphorylation of the src-family kinase lyn and of syk, association of these kinases with the receptor, and activation of kinase activity. Based on the finding that another FcεRIγ-chain associated receptor, FcγRIa, can active both the conventional and the G-protein dependent for of $PI_3$ kinase (124), the present invention examines the capacity for CD89 to activate similar or dissimilar pathway(s). To this end, examinations occur of CD89 receptor specific $[Ca^{2+}]_i$ fluxes and both endocytosis and phagocytosis at low and high levels of receptor cross-linking.

It is appreciated that a form of FcαRI that does not associate with γ-chain can be produced by using a chimeric receptor. To maintain as much of the FcαRI structure as possible, a variant of FcαRI is constructed from which the TM domain is removed and replaced it with CD8. CD8 does not associate with γ-chain. In analogy to the TCR and BCR (125), in some mutants, the magnitude of cross-linking of the receptor complex alters the functional consequences of receptor engagement. In particular, a higher level of receptor cross-linking (induced by IgA+F(ab')$_2$ anti-IgA and/or anti-receptor mAb+F(ab')$_2$ GAM) can result in a distinct pattern of cell activation. Using a biotin-avidin cross-linking system, one can titrate the stoichiometry of receptor aggregations (126).

The ability of different constructs of FcαRI (carrying specific deletions, truncations, and point mutations) to initiate leukocyte cell functions is initially evaluated in cell lines that have been stably transfected with plasmids that express different forms of FcαRI in association with γ-chain. Mutations in the CY domain of FcαRI are guided by for instance functionally important regions and/or motifs in FcαRI for novel associated molecules identified in the two hybrid system. Comparisons are made between cells that stably express on their membrane equivalent levels of native FcαRI (full-length isoform), an FcαRI deletion mutants lacking the CY domain and FcαRI mutants having truncations or point mutations within the CY domain. Controls include cells not transfected with the CD89-expressing plasmid, or with the parent plasmid that does not contain CD89 DNA.

An aspect of present invention is the quantification of polymorphic differences in the induction of both rapid signals,—endocytosis, receptor specific $[Ca^{2+}]_i$ fluxes, activation of tyrosine kinase activity [lyn and syk],—and of FcαRI-specific effector functions. Receptor specific phagocytosis is evaluated using latex microspheres or erythrocytes opsonized with human IgA or anti-FcαRI mAb Fab/F(ab')$_2$ fragments to avoid co-ligation of endogenous Fcγ receptors. Receptor specific stimulation of oxidative metabolism (superoxide production) are quantitated using the same probes as will cytokine production, especially IL-1ra, IL-1, IL-6, TNFα, which are relevant to macrophage function as mediators of inflammatory responses.

Engagement of FcγR is a potent stimulus for the secretion of the pro-inflammatory cytokines IL-1β, IL-6 and TNFα (2) and engagement of FcαRI is known to attenuate release of these cytokines in response to LPS (44). Thus, FcαRI expressing transfectants of the present invention are stimulated with surface bound IgG alone or in combination with surface absorbed IgA. Controls include stimulation with LPS in the presence and absence of surface absorbed IgA. Alternatively, mAb is used to engage distinct receptors on the cell surface. For example, mAb 2.4G2 is used to engage murine FcγRII/FcγRIII and/or murine IgG2a to engage murine FcγRIa with and without anti-FcαRI mAb Fab/F(ab')$_2$ fragments. Heterotypic and homotypic cross-linking is provided by either surface absorbed or solution phase F(ab')$_2$ goat anti-mouse IgG (GAM) or a combination of GAM and anti-human IgA.

Functional significance of SNPs in the coding regions of FcαRI. Peripheral blood neutrophils and monocytes, both of which express CD89, are obtained from genotyped donors and studied ex vivo. Peripheral blood monocytes are also be differentiated in vitro into macrophages resembling those found in tissues and having greater abilities to perform phagocytic functions.

The approach to the functional consequences of the CD89 SNPs varies with the location of the polymorphism in the protein. For polymorphisms in the extracellular region, differences in quantitative binding of IgA ligand to mononuclear and polymorphonuclear cells from genotyped homozygous donors are studied. Binding of both serum IgA and secretory IgA is determined by flow cytometry (127, 128).

Figure 7:
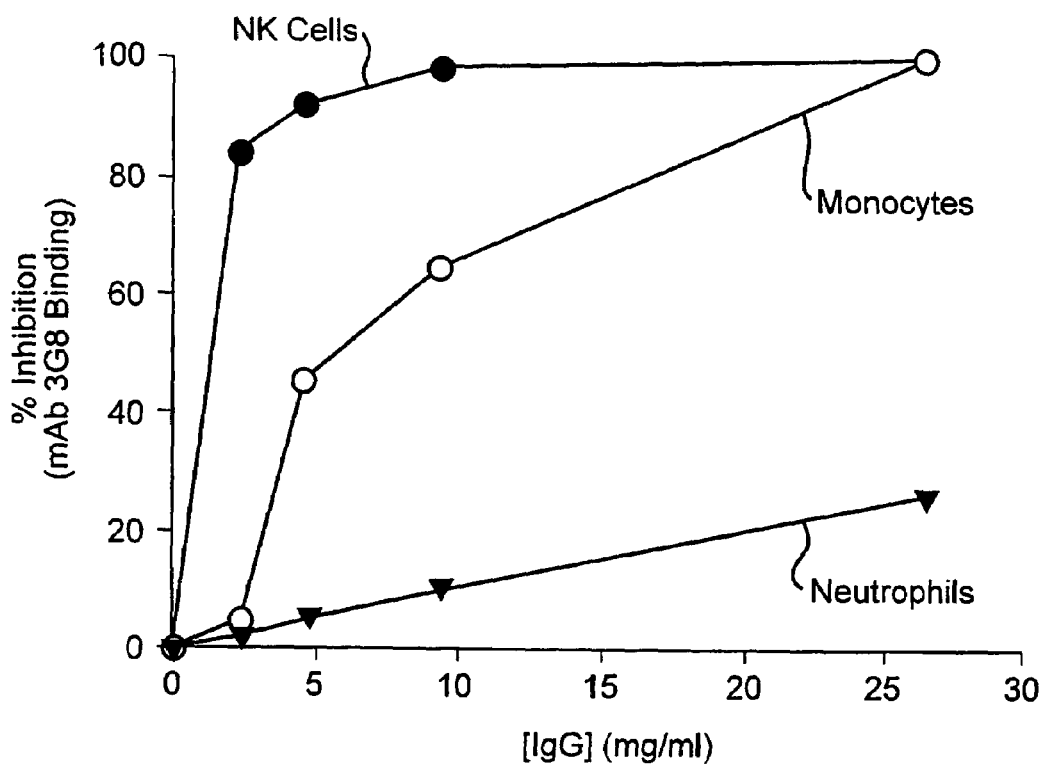
FIG. 7—Blockade of binding of the anti-FcγRIII ligand binding site mAb 3G8 by increasing concentrations of human IgG. The level of mAb 3G8-FITC binding to FcγRIII after incubation with human IgG is shown.

The functional significance of the polymorphisms in the CY domain is determined by examination of FcαRI induced functions. For example, the polymorphisms at positions 245 and 248 alter a casein kinase I phosphorylation site (FIG. 7). For these studies, genotyped homozygous donors and mAb cross-linking are utilized to rule out any impact of other extracellular polymorphisms. Using neutrophils and monocytes from genotyped homozygous disease free donors, a comparison is made between activation of tyrosine kinase activity (lyn and syk) and the induction of cell programs such as receptor specific phagocytosis, oxidative burst, and cytokine production. The release of collagenase from monocytes as an enzyme relevant to periodontal tissue destruction is quantified by ELISA (129). In donors that are identical in the extracellular domains but homozygous for different alleles in the CY domain, IgA is also used as a stimulus, similar to the FcγRIa system for ligand induced stimulation to differ quantitatively from that induced by cross-linked mAb (130).

After definition of functional differences in the donor population, stable transfectants of CD89 of various genotypes are used to more carefully characterize the full impact of each polymorphic residue on the functional properties of the receptors. The choice of cell type is dictated in part by the functional consequences of the polymorphism.

Identification of both pre- and post-translational variations and modifications of FcαRI and their impact on FcαRI function. FcαRI has several splice variants and some investigators have hypothesized that these variants may have different functional capacities (29,30,32,112,113). No systematic evaluation of these splice variants in disease states has been previously undertaken to establish their potential relevance. Similarly, FcαRI is known to be differentially glycosylated in different cell types and in different disease states (128,132). Using the glycoforms of FcγRIIIa as a model (113), the present invention shows that these alterations of glycosylation of FcαRI have different functional properties.

In order to more fully demonstrate the advantages arising from the present invention, the following examples are set forth. It is to be understood that the following is illustrative only and not intended as a limitation on the scope of the invention.

EXAMPLE 1

Isolation of DNA/RNA and cDNA Preparation

Genomic DNA is extracted from leukocytes (in EDTA anti-coagulated whole blood) using with the Puregene DNA isolation kit (Gentra Systems, Minneapolis, Minn.). RNA is isolated from whole blood leukocytes (or Ficoll-Hypaque separated leukocyte fractions) using Triazol RNA isolation solution (Gibco BRL, Gaithersburg, Md.). cDNA is synthesized from 5–10 μg RNA with the SuperScript Preamplification System (Gibco).

EXAMPLE 2 cDNA Sequencing

To facilitate heterozygote detection, a dye primer strategy is used for fluorescence-based automated cycle sequencing of PCR products on an ABI 377. All sequencing primers are designed with an 18 bp M13 sequence tag (ABI PRISM™ Dye Primer Cycle Sequencing -21M13 FS and M13REV FS Ready Reaction Kits (ABI, Foster City, Calif.)). The PCR products are purified with the QIAquick Gel Extraction Kit (Chatsworth, Calif.). The BigDye terminator sequencing reaction chemistry (ABI) is also used to detect heterozygosity in multiple Fc receptors genes including CD89. This chemistry has the advantage of allowing longer sequence reads and does not require the incorporation of additional M13-based sequence in the primers. It is appreciated that all potentially polymorphic residues must ultimately be confirmed by sequencing in both the forward and reverse directions using the dye-primer based strategy.

EXAMPLE 3

Determination of Fcα Receptor Alleles (12–14)

Allele-specific PCR assays are used to genotype donors for the FcαRI alleles illustratively including: FcαRIa (EC1)—87R/87R, FcαRIA (EC1)—92D/92N, FcαRIa (EC2)—132F/132L, FαRI (CY)—245P/245L and FcαRI (CY)—248S/248G alleles. Since there is a finite error rate in any genotyping assay, each assay is corroborated by direct dye-primer based cycle sequencing of at least 40 homozygous donors and an equal number of heterozygous donors. In addition, each assay includes blinded but known genotyped controls to verify the fidelity of the assay. Ambiguities in the assay are resolved by first repeating the allele-specific PCR reaction and then by direct dye-primer based cycle sequencing of genomic DNA samples.

EXAMPLE 4

Amplification of FcαRI cDNA

Two sets of overlapping primers incorporating either the Ml 3 universal or reverse primer sequences at the appropriate 5' ends are used to amplify the entire coding region of the FcαRI cDNA. PCR is performed in a GeneAmp 9600 PCR system with 2.5 U of Taq DNA polymerase (Gibco BRL) using the following cycling conditions: 95° C. for 5 min followed by 35 cycles of denaturation at 94° C. for 30 sec, annealing at 56° C. for 45 sec and extension at 72° C. for one min, followed by a final extension at 72° C. for ten min. The PCR products are gel purified with the QIAquick GEL Extraction Kit (Qiagen). The first set of primers including the underlined M13 sequence amplify from nt 34 in S1 to nt 563 in EC2 (forward primer: 5'-TGTAAA ACG ACG GCC AGT AGC ACG ATG GAC CCC AAA CAG-3' (SEQ ID NO. 1); reverse primer: 5'-CAGGAAACAGCTATGACC GGT GTT CCC CAC TTT GGT GC-3' (SEQ ID NO. 2). The second set of primers amplify from nt 458 in EC1 to nt 934 in the 3'-untranslated region (forward primer: 5'-TGTAAA ACG ACG GCC AGT AGA ATA TTT CCC TCA CGT GC-3' (SEQ ID NO. 3); reverse primer: 5'-CAGGAAACAGCTATGACC CTG GCT CCT CTC TGC CTT CAC-3' (SEQ ID NO. 4)).

EXAMPLE 5

Yeast 2-Hybrid System

The yeast two-hybrid system based on the Gal4 transcriptional activator will use our cloned 41 amino acid CD89 cytoplasmic domain in the pGBT9 vector containing the DNA binding domain of the GAL4 transcriptional activator (BD-CD89). Screening the BD-CD89 is performed against a cDNA expression library isolated from total unstimulated human PBL, a cDNA library from EBV infected pooled human PBL and a cDNA library from PHA-stimulated PBL all of which are cloned into the pACT vector with the Gal4 activation domain. A U937 myeloid cDNA library in pACT is also constructed for this screening purpose. Using strain HF7c yeast His/Trp/Leu auxotrophs, double transformants (BD-CD89+AD construct) are screened on Trp⁻, Leu⁻, His⁻ dropout plates containing 10 mM 3-amino-triazole to select for positive interactions between the CD89 cytoplasmic domain and the fusion protein encoded by AD-cDNA. Growth positive colonies are screened secondarily for LacZ activity, the second reporter gene under the control of the Gal4 promoter. The plasmids containing the AD-cDNA construct is recovered from growth (+), LacZ (+) colonies by transforming into *E. coli* HB101, harvested, sequenced, and compared to information currently in GenBank. Likely candidates, identified by multiple isolates and by putative biology, are directly rescreened (BD-CD89+AD-candidate cDNA), and, if positive, are then tested for protein—protein interactions in co-immunoprecipitations from whole cell lysates and in GST-fusion protein (Pharmacia) affinity matrix/whole cell lysate interactions. Positive candidates in the two hybrid screen which are also positive for bona fide protein—protein interactions are deemed to be true associations. An unstimulated PBL library in the DupLEX-A™ system (Origene) also successfully screened with a BD-FcγRIIIa cytoplasmic domain construct. The DupLEX-A™ system has the advantage of reduced false positives and the presence of an HA tag downstream of the B42 activation protein for subsequent purification.

EXAMPLE 6

Transfection

Using the pRC/CMV (Invitrogen) expression vector, COS-7 cells (CaPO4, glycerol shock and chloroquine; and lipofectamine), UC729.6 cells (electroporated using 280V and 960° F. across 0.4 cm) and P388D1 (CaPO4, glycerol shock and chloroquine and lipofectamine) have been transiently, and transfected P3881D1 cells using both CaPO4, glycerol shock and chloroquine and lipofectamine have been stably transfected. For stable transfectants, the FACS Vantage is used for flow cytometry with receptor-specific mAbs to cell sort for subpopulations expressing quantitatively different levels of receptor. It is appreciated that comparable levels of transfectant expression are required in studying differences in function by different receptor constructs.

EXAMPLE 7

Receptor and Isoform Cloning

Products generated by PCR are separated by electrophoresis through low melting point agarose. To generate clones for sequencing the TA Topoisomerase Cloning system (Invitrogen) is used. For mammalian expression, blunt end ligated PCR product is inserted into vector pRC/CMV (Invitrogen), transformed competent *E. coli* with ampicillin based selection and confirmed plasmid integration with plasmid isolation and restriction fragment pattern analysis. Newer strategies for eukaryotic expression including the use of undirectional TA cloning strategies and the expression vector pCR3-Uni which uses the immediate-early CMV promoter (Invitrogen) are also suitable.

EXAMPLE 8

Construction of GST Fusion Proteins

To generate glutathione-S-transferase (GST) fusion constructs for expression in *E. coli*, PCR amplified cDNA or cDNA fragments are subcloned into the BamHI-EcoRI site of the pGEX-2T vector (Pharmacia Biotech). Following transformation into *E. coli* DH5a, fusion protein is induced in log phase cultures by the addition of 0.1 mM isopropyl-b-d-thiogalactopyranoside and purified by incubation of soluble lysates with glutathione-sepharose beads.

EXAMPLE 9

Site-Directed Mutagenesis

To generate site-specific mutations, oligonucleotide primers containing the desired mutation(s) are used for PCR of α-chain cDNA. With the PCR Site-directed Mutagenesis System (Life Technologies), the amplified fragments are cloned in plasmid pAMP2 using Uracil DNA glycosylase and used to transform competent *E. coli*. Mutations are verified by sequencing and then cloned into an appropriate eukaryotic expression vector such as pRC/CMV to generate stable transfectants of P388D1 cells.

EXAMPLE 10

Statistics

Experimental data is evaluated statistically by means of StatView (Abacus Concepts, Inc., Berkeley, Calif.) or InStat (GraphPad Software, San Diego, Calif.) programs run on computers. Student's t tests for comparison of means of two data sets, ANOVA for multiple comparisons, and regression/correlation analyses will be performed as appropriate. Simple transformations (e.g. logarithmic) will be performed as needed to improve the distribution characteristics of the data ('normalizing'). Non-parametric methods are also available.

EXAMPLE 11

Alternative Identification Method for FcαRIa Genotype

Alternative methods of genotyping are also operative, such as the oligonucleotide ligation assay (OLA). In this genotyping assay, the polymorphic residue is within the PCR amplicon. Three oligonucleotides are then added; one that is immediately 3' to the polymorphic residue, a fluorescently labeled oligonucleotides that is complementary to one allele at the 3' end and a fluorescently labeled third oligonucleotides that is complementary to the other allele at the 3' end. The two labeled primers need to be of different lengths (different by >2 nucleotides) and can be labeled with the same or different fluorescent probes (such as 6-fam and tet for detection on the ABI377). This technique is now widely used for analysis of mutations in the cystic fibrosis gene (63).

EXAMPLE 12

Determination of Cytokine Promoter Alleles

While some microsatellites associated with various cytokine genes have been identified, a systematic search of the 5' promoter region reference sequences for novel SNPs is not available (4,45–51,113). However, SNPs occur with reasonable frequency (approximately 1 per 500–1000 bp) and at least some of these SNPs are of biological significance. Identifying such SNPs and developing both microsatellite and SNP assays for characterization of a clinical population use the techniques of Examples 1–5, as well as other techniques conventional to the art. Examples of cytokine genes are given:

| Gene | Length of 5'<br>Promoter Reporter | Genbank<br>Accession No. | Reference |
|------|-----------------------------------|--------------------------|-----------|
| TNFα | 1,178 bp | L11698 | 133 |
| IL-1α | 1,413 bp | X03833 | 134 |
| IL-1β | 4,991 bp | U26540 | 135 |
| IL-1ra | 5,953 bp | X64532 | 136 |
| IL-6 | 1,222 bp | Y00081 | 137 |
| IL-10 | 4,181 bp | X78437 | 138, 139 |

EXAMPLE 13

General Protein Techniques

Techniques for immunoprecipitation, SDS-PAGE, Western blotting, and related methods are known to the art. MAb to FcγR and FcαR (CD89) are commercially available (Medarex, Biodesign International, Pharmingen). MAb and polyclonal Ab to src-family tyrosine kinases and syk are also available (UBI, Santa Cruz Biochemicals, Signal Transduction Labs).

EXAMPLE 14

γ-Chain Co-Immunoprecipitation

Using detergent lysing conditions that have been shown to preserve the non-covalent interaction between γ-chain and Fc receptor (35,97), cells are lysed in buffer containing 1% digitonin (Wako) and protease inhibitors. CD89 is immunoprecipitated with anti-receptor mAb using standard techniques. Following SDS-PAGE separation and blotting, γ-chain will be detected with a rabbit polyclonal anti-γ-chain Ab that recognizes both human and murine γ-chain.

EXAMPLE 15

Phosphotyrosine Analysis

Stimulated or control neutrophils are lysed as previously described in Example 8 with the addition of the phosphatase inhibitor sodium orthovanadate (0.4 mM). Anti-phosphotyrosine or anti-target immunoprecipitates are separated by SDS-PAGE and transferred to nitrocellulose membranes essentially as described (126). Blots are detected with either anti-target Ab or anti-phosphotyrosine (mAb 4G10 or PY20) and detected with a HRP conjugated sheep-anti-mouse IgG followed by detection with an enhanced chemiluminescence reagent set (Amersham). In vitro kinase assays are performed after immunoprecipitation by washing the immune complexes in kinase buffer (20 mM MOPS, 5 mM $MgCl_2$) and adding 10–15 $\mu Ci$ $\gamma^{32}P$-ATP and unlabeled ATP. After a 1–15 min incubation, the immune complexes are spun, washed and separated by SDS-PAGE (140).

EXAMPLE 16

Collagenase Assay

The release of collagenase (MMP-1) from human neutrophils or monocytes is analyzed with the use of a standard sandwich ELISA (129), using plates coated with mAb COMY4A2. After incubating with samples of monocyte supernatant or standards, bound collagenase is detected by means of monoclonal antibody an HRP-conjugated polyclonal anti-collagenase antibody 647.

EXAMPLE 17

Cytokine Assays

Levels of cytokines IL-1, IL-1ra, IL-6, and TNFα secreted in culture media are assayed by ELISA, using polyclonal (goat) and monoclonal anti-human cytokine reagents (R&D Systems, Minneapolis, Minn.). For murine cytokines secreted by transfected cells, anti-mouse cytokine reagents is obtained from Pharmingen (San Diego), or R&D Systems. The assays are calibrated against standards obtained from the same sources.

EXAMPLE 18

Purification of Igs

Human serum Igs are purified by chromatography using anion exchange (Mono Q), molecular sieve (Superose 6 or 12, or Sephacryl S-300), affinity (jacalin-HiTrap for IgA1; protein G-HiTrap for IgG), and immunoadsorbent (anti-IgM-HiTrap) columns in an FPLC apparatus (Pharmacia Biotech, Piscataway, N.J.) or conventional columns. IgA subclasses are separated by means of a jacalin-HiTrap column which retains IgA1 while IgA2 passes; IgA1 is then recovered by elution with 0.1 M melibiose. Monomeric and polymeric IgA are separated by HPLC on a Biosep Sec-S3000 column (Phenomenex, Torrance, Calif.), or for larger quantities by FPLC on a Sephacryl S-300 Hi-Prep column. All these procedures are frequently used in this laboratory, and are capable of achieving >99% purity of Ig isotypes (141,142). Purity and concentration are assessed by SDS-PAGE and ELISA (see above).

IgA myeloma proteins of both subclasses and in different molecular forms (monomers and a variety of polymeric configurations) are available from a collection kept by Dr. Jiri Mestecky. These are purified by essentially the same procedures as described for normal serum IgA.

EXAMPLE 19

Assay of Ig and Antibodies (ELISA)

To assay Igs, the plates are coated with anti-Ig antibodies of the desired specificity (Dako Corp., Carpinteria, Calif.), at optimal levels (1–10 ug/ml). The plates are blocked with 0.15% Tween 20 in PBS, and serially diluted samples, starting from a dilution appropriate to the sample and the expected analyte concentration, are applied overnight. Bound Ig is detected by means of peroxidase-conjugated antibody to the analyte, diluted to the previously determined optimal level in each case (usually 1:1,000–1:5,000), and applied for 4 h. When IgA subclasses are assayed, the bound Ig is detected with monoclonal anti-IgA1 or anti-IgA2 antibodies (Nordic Immunological Labs., Capistrano Beach, Calif.), followed by peroxidase-conjugated anti-mouse Ig (Southern Biotechnology, Inc., Birmingham, Ala.). Finally, the color developed with a substrate of o-phenylenediamine (0.5 mg/ml) plus 1 mM $H_2O_2$ after 15 min is read at 490 nm in an ELISA plate reader (MRX; Dynatech Laboratories, Chantilly, Va.) interfaced to a computer for data retrieval and processing. Controls include the use of uncoated (blocked) wells, and coated wells treated with all reagents but not exposed to analyte sample. All determinations are performed

EXAMPLE 20

Cell Preparations

PMN, myeloid cells and monocytes are prepared as described (144) using discontinuous ficoll/hypaque density gradient centrifugation. Monocytes are purified by adherence to 100 mm tissue culture plates or directly in 96 well plates for use in functional assays for 90 min at 37° C./5% $CO_2$ (144). The non-adherent lymphocytes are recovered by rinsing in medium. When appropriate, adherent monocytes are collected by treatment for 2 min. with 0.1% EDTA in Dulbecco PBS, and the cells washed and resuspended in medium. Alternatively, monocytes are allowed to form homotypic clumps by incubation 4° C. (145). Clumped monocytes are then sedimented through a FCS cushion at 1xg, washed and gently dispersed. Purities >90% can routinely be achieved with these techniques (144). The purity of monocytes is assessed by staining for non-specific esterase or with fluorochrome-labeled antibody to CD14. Cells are counted using 0.1% trypan blue to assess viability. For studies requiring large numbers of cells, buffy coat units from the blood bank are used which can yield in excess of $10^8$ monocytes.

Eosinophils are isolated from the granulocyte fraction of citrated normal human blood (obtained by centrifugation through Percoll SG 1.082). Erythrocytes are removed by hypotonic lysis in water. CD16+ cells (mainly neutrophils, also NK cells) are removed by magnetic sorting (MACS column, Miltenyi Biotec) using anti-CD16 antibody coupled to magnetic beads. The yield is ~98% pure esosinophils (146).

EXAMPLE 21

Cell Culture

Cells are cultured in RPMI 1640 medium supplemented with 10% fetal calf serum, L-glutamine, non-essential amino acids, and antibiotics (complete medium) at 37° C. in humidified 5% $CO_2$/air (123,144).

EXAMPLE 22

Flow Cytometry

Standard analytical flow cytometry (one to four colors) is performed on a FACScan flow cytometer (Becton-Dickinson). Sorting of transfected cell lines is performed on a FACS-Vantage (Becton-Dickinson). The instrument is capable of routine sterile sorts into tubes or tissue culture plates.

EXAMPLE 23

Phagocytosis Assay

The phagocytic response of transfected murine cells or human peripheral blood monocytes are assessed by flow cytometry (41). Fluorescent 1 um microspheres (Polysciences, Warrington, Pa.) are coated with human IgA or IgG, or with mAb to CD89 at 25 ug/$10^9$ microspheres in PBS at 4° C. for 16 h and blocked with 1% human serum albumin (HAS) in PBS. Control microspheres are coated with HSA only. Alternatively, microspheres are coated with anti-human light chain F(ab)'2 to capture human Ig in a more physiological presentation of the Fc region for receptor engagement. The coated microspheres are added to the cultured monocytes at a ratio of 10 microspheres/monocytes for 4 h at 37° C. in 5% $CO_2$, and the cells are collected for analysis by flow cytometry (FACScan, Becton Dickinson). Alternatively, biotinylated anti-receptor mAb or Ig are bound to streptavidin saturated biotinylated PKH26-labeled E as we have previously reported (147). The opsonized E are mixed with phagocytes at a ratio of 50:1, incubated for varying periods of time, and the non-internalized E are removed by hypotonic lysis. Phagocytosed E are then quantitated by flow cytometry.

EXAMPLE 24

Superoxide Assay

The production of superoxide ($O2^-$) by transfected cells of human monocytes is determined by superoxide dismutase (SOD)-inhibitable cytochrome C reduction (140). Cytochrome C (Sigma Chemical Corp., St. Louis, Mo.) is added to the monocyte culture medium, with or without SOD (Sigma), and the amount of reduced cytochrome C is measured by absorbance at 550 nm.

EXAMPLE 25

Analysis of Changes in Intracellular $Ca^{2+}$ Levels

Indo-1 (for cuvette based and flow cytometric [$Ca^{2+}$] determination) or Fura-2 (for single cell [$Ca^{2+}$] determination), both calcium binding fluorescent dyes whose spectral properties change with binding of free $Ca^{2+}$, is used to measure changes in intracellular calcium concentrations ([$Ca^{2+}$]$_1$) (4,122,123,148). Cuvette based batch analysis is performed in an SLM-8000 spectofluorometer and flow cytometric analysis is performed in the FACS-Vantage equipped with UV-excitation.

EXAMPLE 26

Novel Molecular Associations with the Cytoplasmic Domain of FcαRI

Using the yeast two-hybrid system based on the GAL4 transcriptional activator, the entire 41 amino acid cytoplasmic domain of CD89 in-frame with a 6-gly linker is cloned into the pGBT9 vector containing the DNA binding domain of the GAL4 transcriptional activator. Using this binding domain construct expressing the cytoplasmic domains of FcαRI, screening against cDNA expression libraries that have been cloned into the pACT vector with the GAL4 activation domain (AD) occurs. Cloned cDNA libraries derived from total unstimulated human PBMC, EBV transformed pooled human PBMC and PHA stimulated human PBMC are utilized. Using strain HF7c yeast His auxotrophs, double transformants (BD-CD89+AD-cDNA construct) are screened on Trp⁻, Leu⁻, His⁻ dropout plates containing 10 mM 3-amino-triazole to select for positive interactions between the CD89 cytoplasmic domain and the fusion protein encoded by AD-cDNA. Growth positive colonies are then screened secondarily for LacZ, the second reporter under the control of the GAL4 promoter. The AD-cDNA construct plasmid is recovered from growth (+), LacZ (+) colonies by transforming into E. coli, harvested, sequenced, and compared to information currently in GenBank. Likely candidates, identified by multiple isolates and by putative biology, are directly rescreened (BD-CD89+AD-candidate cDNA), and, if positive, are then tested for protein—protein interactions in co-immunoprecipitations from whole cell lysates and in GST-fusion protein affinity matrix/whole cell lysate interactions. Positive candidates identified in the two hybrid screen which are also positive for bonafide protein—protein interactions are deemed to be true associations. Subsequent studies depend on the structural and biological nature of the protein(s) identified, but such studies include truncations/point mutations to identify the regions in CD89 and in the interacting protein that mediate the interaction (in both the yeast two-hybrid system and/or transfection of mutant forms into mammalian cells), scanning laser confocal microscopy to identify association in intact cells, and functional studies to demonstrate the biological importance of the interaction.

All positives, therefore, must be evaluated for direct protein—protein interactions in in vivo systems. Definition of these interactions requires suitable reagents. When mAb or polyclonal Abs directed against the interacting protein(s) are not immediately available, the initial characterization of the protein-FcαRI interaction with a GST-fusion protein and polyclonal anti-GST Abs is carried out. Anti-CD89 monoclonal Abs are available, and rabbit polyclonal Abs directed against proteins identified in prior yeast two-hybrid screens are also readily made using conventional techniques.

The yeast two-hybrid system is best suited for higher affinity protein—protein interactions which are not phosphorylation dependent. Therefore, while true positives are highly informative, they do not comprise the entire repertoire of interacting proteins. The ability to identify true positives also depends on the suitability of the screening library. These libraries are particularly useful in identifying proteins that interact with FcγR expressed in myeloid and lymphoid cells. When difficulties are encountered with the GAL4-based system, the DupLex-A™ system has several potential advantages including a reduction in the number of false positives and ease of co-immunoprecipitation with the HA tag downstream of the B42 activation protein.

EXAMPLE 27

Identification of Novel SNPs in FcαRI

Through the examination of cDNA derived from disease free-individuals, the present invention identifies multiple single nucleotide polymorphisms in the coding region of the CD89 gene. Indeed, there are SNPs in each of the three exons encoding the EC1, EC2 and the TM/CY domains (FIG. 4).

Amplification and sequencing of the CD89 cDNA is complicated by the presence of multiple alternatively spliced products. Currently available evidence suggests the presence of at least nine different alternatively spliced transcripts of FcαRI (29,30,32,112,131). Many of these transcripts are co-expressed in the same cell type. Accordingly, the present invention amplifies the FcαRI cDNA in two overlapping segments and gel purifies fragments corresponding to the full length FcαRI transcript (expressing S1, S2, EC1, EC2 and TM/CY). The 5' segment is amplified with a pair of primers located in the S1 region and the EC2 region (nt 34 to 563). The 3' segment of the FcαRI cDNA is amplified with a pair of primers located in EC1 and the 3'-untranslated region (nt458 to 934). The gel-purified PCR amplified segments are cycle-sequenced from both directions.

The sequencing of a specific PCR-amplified FcαRI cDNA may be complicated by the presence of multiple splice variants that cannot be adequately resolved by agarose gel electrophoresis. For example, if there is a splice variant that does not express exon S2 (36 nt), which allows co-purification with wild type FcαRI. Sequencing of the 5' segment in the forward direction is then not possible. However, in this situation, reverse direction sequencing up to the S2-EC 1 splice site yields the necessary information.

EXAMPLE 28

Expression of FcαRIb and FcαRI Splice Variants in Patients with PD

A protein product of a sequence is studied by biosynthetically labeling cells expressing the sequence with $^{35}$S-methionine, the cells are lysed and anti-CD89 mAb is used for immunoprecipitation from both cell supernatants and from cell lysates. Following deglycosylation with endoglycosidase F (N-Glycanase®), the putative product is resolvable from the larger a isoforms on a higher percentage polyacrylamide gel.

Quantitative variations in the level of expression of these alternatively spliced forms of the FcαRI mRNA are performed by RNAse protection using a $^{32}$P-labeled riboprobe that contains a portion of EC2 and a portion of the TM/CY domain. This strategy allows for resolution of the a1, a2, a3 and b forms by differences in electrophoretic mobility.

EXAMPLE 29

Examination of FcαRI Post-Translational Processing in Relation to IgA Binding

FcαRI expressed on different cell types has distinct molecular weights which resolve to identical protein cores upon removal of N-linked oligosaccharides. For example, the mature proteins in $^{125}$I-labeled anti-CD 89 immunoprecipitates from PMN and eosinophils are each heterogeneous but very distinct in apparent Mr, 55–75 kD vs. 70–100kD respectively (128). Upon treatment with endoglycosidase F, these forms reduce to a common major band of 32 kD with a minor 36 kD band evident from PMN. The mol wt of FcαRI from human monocytes and U937 cells are analyzed in comparison to PMN and eosinophils with and without endoglycosidase F (N-glycanase™) treatment as we have previously done for human FcγRIII (144).

Two different independent approaches are used to analyze the quantitative aspects of IgA binding. First, the concentration dependence of human monomeric IgA, dimeric IgA, secretory IgA, and IgA1/IgA2 ligand in blocking the binding of the anti-ligand binding site mAb My43 is determined. This approach has been used to define relative difference in affinity between the NK cell and macrophage glycoforms of FcγRIIIa (CD16)(17). The alternative, more direct measure of binding affinity is performed with $^{125}$I-labeled ligands and saturation binding isotherms. Using the technique of Weisbart et al. (149), the binding of 0–10 pmol of $^{125}$I-labeled ligand to 5×10$^6$ cells for 24 h at 4° C., in the presence and absence of excess unlabeled ligand, is measured. As an independent approach to determining of glycosylation alters binding of IgA, cells are treated with neuraminidase (150, 151) and binding of IgA is analyzed (151).

EXAMPLE 30

Modification of FcαRI Glycosylation in Patients with PD and RA

FcαRI is immunoprecipitated with anti-receptor mAb and analyzed by SDS-PAGE and blotting with a variety of informative biotinylated lectins. PMN and monocyte FcαRI are analyzed by lectin reactivity and comparisons are made between patients with PD, RA, IgA nephropathy and disease free individuals.

The present invention demonstrates the CD89 polymorphism can be exploited as a diagnostic assay for determining susceptibility to and/or severity of various diseases involving IgA. The present invention further demonstrates a process through which the use of genotyping and/or phenotyping to assist in defining disease prognosis.

Any patents or publications mentioned in the specification are indicative of the levels of those skilled in the art to which the invention pertains. These patents and publications are herein incorporated by reference to the same extent as if each individual publication was specifically and individually indicated to be incorporated by references.

REFERENCES

1. Kimberly R P, Salmon J E, Edberg J C. Receptors for immunoglobulin G. Molecular diversity and implications for disease. Arthritis Rheum 38:306–314, 1995.
2. Hulett M D, Hogarth P M. Molecular basis of Fc receptor function. Adv Immunol 57: 1–127, 1994.
3. Daeron M. Fc receptor biology. Annu Rev Immunol 15: 203–234, 1997.
4. Wu J, Edberg J C, Redecha P D, Bansal V, Guyre P M, Coleman K, Salmon J E, Kimberly R P. A novel polymorphism of FcγRIIIa (CD16) alters receptor function and predisposes to autoimmune disease. J Clin Invest 100: 1059–1070, 1997.
5. Clark M R, Clarkson S B, Ory P A, Stollman N, Goldstein I M. Molecular basis for a polymorphism for human Fcγ receptor II on human monocytes. J Immunol 143: 1731, 1989.
6. Warmerdam P A M, van de Winkel J G J, Gosselin E J, Capel P J A. Molecular basis for a polymorphism of human Fcγ receptor II (CD32). J Exp Med 172, 19, 1990.
7. Clark M R, Stuart S G, Kimberly R P, Ory P A, Goldstein I M. A single amino acid distinguishes the high-responder from low-responder form of Fc receptor II on human monocytes. Eur J Immunol 21: 1911–1916, 1991.
8. Edberg J C, Wainstein E, Wu J, Csemok E, Sneller M C, Hoffman G S, Keystone E C, Gross W L, Kimberly R P. Analysis of FcγRII gene polymorphisms in Wegener's Granulomatosis. Exp Clin Immunogenetics 14:183–195, 1997.
9. Gibson A, Wu J, Edberg J C, Kimberly R P. Fcγ receptor polymorphisms: Insights into pathogenesis. In: *Lupus: Molecular and Cellular Pathogenesis*. Kammer G, Tsokos G (eds). Humana Press, 1998, in press.
10. Warmerdan P S, van de Winkel J G, Vlug A, Westerdaal N A, Capel P J. A single amino acid in the second Ig-like domain of the human Fcγ receptor II is critical for human IgG2 binding. J Immunol 147: 1338–1343, 1991.
11. Salmon J E, Edberg J C, Kimberly R P. Fcγ receptor III on human neutrophils: Allelic variants have functionally distinct capacities. J Clin Invest 85: 1287, 1990.
12. Salmon J E, Edberg J C, Brogle N L, Kimberly R P. Allelic polymorphisms of human Fcγ receptor IIA and Fcγ receptor IIIB: Independent mechanisms for differences in human phagocyte function. J Clin Invest 89:1274–1281, 1992.
13. Parren P W, Warmerdam P A, Boeije L C, Arts J, Westerdaal N A, Vlug A, Capel P J, Aarden L A, van de Winkel J G. On the interaction of IgG subclasses with the low affinity FcγRIIa (CD32) on human monocytes, neutrophils, and platelets. Analysis of a functional polymorphism to human IgG2. J Clin Invest 90: 1537–1546.
14. Cambier J C. Antigen and Fc receptor signaling. The awesome power of the immunoreceptor tyrosine-based activation motif (ITAM). J Immunol 155: 3281–3285, 1995.
15. Salmon J E, Brogle N L, Edberg J C, Kimberly R P. Fc gamma receptor III induces actin polymerization in human neutrophils and primes phagocytosis mediated by Fc gamma receptor II. J Immunol 146: 997–1004, 1991.
16. Edberg J C, Salmon J E, Kimberly R P. Functional capacity of FcγRIII on neutrophils. Immunological Res 11: 239–251, 1992.
17. Salmon J E, Millard S S, Brogle N L, Kimberly R P. Fcγ receptor IIIb enhances Fcγ receptor IIa function in an oxidant-dependent and allele-sensitive manner. J Clin Invest 95: 2877–2885, 1995.
18. Perussia B, Dayton E T, Lazarus R, Fanning V, Trinchieri G. Immune interferon induces the receptor for monomeric IgG1 on human monocytic and myeloid cells. J Exp Med 158: 1092–1113, 1983.
19. Guyre P M, Morganelli P M, Miller R. Recombinant immune interferon increase immunoglobulin G Fc receptors on cultured human mononuclear phagocytes. J Clin Invest 72: 393–397, 1983.
20. te Velde A A, de Waal Malefijt R, Huijbens R J, de Vries J E, Figdor C G. IL-10 stimulates monocyte Fc gamma R surface expression and cytotoxic activity. Distinct regulation of antibody-dependent cellular cytotoxicity by IFN-gamma, IL-4, and IL-10. J Immunol 149: 4048–4052, 1992.
21. Daëron M, Latour S, Malbec O, Espinosa E, Pina P, Pasmans P, Fridman W H. The same tyrosine based inhibition motif, in the intracytoplasmic domain of FcγRIIb, regulates negatively BCR-, TCR- and FcR-dependent cell activation. Immunity 3:635–646, 1995.
22. Muta T, Kurosaki T, Misulovin Z, Sanchez M, Nussenzweig M C, Ravetch J V. A 13-amino acid motif in the cytoplasmic domain of FcγRIIb modulates B-cell receptor signaling. Nature 368:70–73, 1994.
23. Tridandapani S, Kelley T, Pradhan M, Cooney D, Justement L B, Coggeshall K M. Recruitment and phosphorylation of SH2-containing inositol phosphatase and Shc to the B-cell Fc gamma immunoreceptor tyrosine-based inhibition motif peptide motif. Mol Cell Biol 17: 4305–4311,1997.
24. Ono M, Okada H, Bolland S, Yanagi S, Kurosaki T, Ravetch J V. Deletion of SHIP or SHP-1 reveals two distinct pathways for inhibitory signaling. Cell 90: 293–301, 1997.
25. Ono M, Bolland S, Tempst P, Ravetch J V. Role of the inositol phosphatase SHIP in negative regulation of the immune system by the receptor FcγIIB. Nature 383: 263–266, 1996.
26. Gupta N, Scharenberg A M, Burshtyn D N, Wagtmann; N, Lioubin M N, Rohrschneider L R, Kinet J P, Long E O. Negative signaling pathways of the killer cell inhibitory receptor and FcγRIIb1 require distinct phosphatases. J Exp Med 186: 473–478, 1997.

27. Morton H C, Schiel A E, Janssen S W J, van de Winkel J G J. Alternatively spliced forms of the human myeloid Fcα receptor (CD89) in neutrophils. Immunogenetics 43: 246–247, 1996.

28. Patry C, Sibille Y, Lehuen A, Monteiro R C. Identification of Fcα receptor (CD89) isoforms generated by alternative splicing that are differentially expressed between blood monocytes and alveolar macrophages. J. Immunol. 156: 4442–4448, 1996.

29. Pleass R J, Andrews P D, Kerr M A, Woof J M. Alternative splicing of the human IgA Fc receptor CD89 in neutrophils and eosinophils. Biochem J 318: 771–777, 1996.

30. Reterink T J F, Verweij C L, van Es L A, Daha M R. Alternative splicing of IgA Fc receptor (CD89) transcripts. Gene 175: 279–280, 1996.

31. Morton H C, Van Egmond M, van de Winkel J G J. Structure and function of human IgA Fc receptors (FcαR). Crit. Rev. Immunol. 16: 423–440, 1996.

32. van Dijk T B, Bracke M, Caldenhoven E, Raaijmakers J A M, Lammers J W J, Koenderman L, de Groot R P. Cloning and characterization of FcαRb, a novel Fcα receptor (CD89) isoform expressed in eosinophils and neutrophils. Blood 88: 4229–4238, 1996.

33. Monteiro R C, Kubagawa H, Cooper M D. Cellular distribution, regulation, and biochemical nature of an Fcα receptor in humans. J. Exp. Med. 171: 597–613, 1990.

34. Monteiro R C, Cooper M D, Kubagawa H. Molecular heterogeneity of Fcα receptors detected by receptor-specific monoclonal antibodies. J. Immunol. 148: 1764–1770, 1992.

35. Morton H C, Van den Herik-Oudijk I E, Vossebeld P, Snijders A, Verhoeven A J, Capel P J A, Van de Winkel J G J. Functional association between the human myeloid immunoglobulin A Fc receptor (CD89) and FcR gamma chain—Molecular basis for CD89/FcR gamma chain association. J. Biol. Chem. 270: 29781–29787, 1995.

36. Stewart W W, Mazengera R L, Shen L, Kerr M A. Unaggregated serum IgA binds to neutrophil FcαR at physiological concentrations and is endocytosed but cross-linking is necessary to elicit a respiratory burst. J. Leukocyte Biol. 56:481–487, 1994.

37. Mackenzie S J, Kerr M A. IgM monoclonal antibodies recognizing FcαR but not FcγRIII trigger a respiratory burst in neutrophils although both trigger an increase in intracellular calcium levels and degranulation. Biochem. J. 306: 519–523, 1995.

38. Patry C, Herbelin A, Lehuen A, Bach J F, Monteiro R C. Fcα receptors mediate release of tumour necrosis factor-α and interleukin-6 by human monocytes following receptor aggregation. Immunology 86: 1–5, 1995.

39. Reterink T J F, Levarht E W N, Klar-Mohamad N, Van E s L A, Daha M R. Transforming growth factor-beta 1 (TGF-b1) down-regulates IgA Fc-receptor (CD89) expression on human monocytes. Clin. Exp. Immunol. 103: 161–166, 1996.

40. Russell M W, Reinholdt J, Kilian M. Anti-inflammatory activity of human IgA antibodies and their Fab fragments: inhibition of IgG-mediated complement activation. Eur. J. Immunol. 19: 2243–2249. 1989.

41. Nikolova E B, Russell M W. Dual function of human IgA antibodies: inhibition of phagocytosis in circulating neutrophils and enhancement of responses in IL-8-stimulated cells. J. Leukocyte Biol. 57: 875–882, 1995.

42. Russell M W, Sibley D A, Nikolova E B, Tomana M, Mestecky J. IgA antibody as a non-inflammatory regulator of immunity. Biochem. Soc. Trans. 25: 466–470, 1997.

Russell M W, Kilian M, Lamm M E. Biological activities of IgA. In: *Mucosal Immunology*, 2nd Edition, Ogra P L, Mestecky J, Lamm M E, Strober W, McGhee J R, Bienenstock J (eds.) Academic Press, San Diego (in press, 1998).

43. Wolf H M, Fischer M B, Puhringer H, Samstag A, Vogel E, Eibl M M. Human serum IgA downregulates the release of inflammatory cytokines (tumor necrosis factor-α, interleukin-6) in human monocytes. Blood 83: 1278–1288, 1994.

44. Wolf H M, Hauber I, Gulle H, Samstag A, Fischer M D, Ahmad R U, Eibl M M. Anti-inflammatory properties of human serum IgA: induction of IL-1 receptor antagonist and FcαR (CD89)-mediated down-regulation of tumour necrosis factor-alpha (TNFα) and IL-6 in human monocytes. Clin Exp Immunol 105: 537–543, 1996.

45. Lamster I B, Smith Q T, Celenti R S, Singer R E, Grbic J T. Development of a risk profile for periodontal disease: microbial and host response factors. J. Periodontol. 65: 511–520, 1994.

46. Miyazaki A, Kobayashi T, Suzuki T, Yoshie H, Hara K. Loss of Fcγ receptor and impaired phagocytosis of polymorphonuclear leukocytes in gingival crevicular fluid. J. Periodont. Res. 32: 439–446, 1997.

47. Williams R C. Periodontal disease. New Engl J Med 322: 373–382, 1990.

48. Van Dyke T E, Lester M A, Shapira L. The role of the host response in periodontal disease progression: implications for future treatment strategies. J Periodontol 64: 792–806, 1993.

49. Page R C. The role of inflammatory mediators in the pathogenesis of periodontal disease. J Periodont Res 26: 230–242, 1991.

50. Genco R J. Host responses in periodontal disease: current concepts. J Periodontol. 63: 338–355, 1992.

51. Socransky S S, Haffajee A D. The bacterial etiology of destructive periodontal disease: current concepts. J Periodontol 63: 322–331, 1992.

52. Slots J, Listgarten M A. *Bacteroides givgivalis, Bacteroides intermedius* and *Actinobacillus actinomycetemycomitans* in human periodontal diseases. J Clin Periodontol 15: 1988.

53. Potempa J, Pike R, Travis J. The multiple forms of trypsin-like activity present in various strains of *Porphyromonas gingivalis* are due to the presence of either Arg-gingipain or Lys-gingipain. Infect Immunity 63: 1176–1182, 1995.

54. Wingrove J A, Discipio R G. Chen Z, Potempa J, Travis J, Hugli T E. Activation of complement components C3 and C5 by a cytsteine protease (gingipain-1) from *Porphyromonas* (*Bacteroides*) *gingivalis*. J Biol Chem 267: 18902–18907, 1992.

55. Schenkein H A, Fletcher H M, Bodnar M, Macrina F L. Increased opsonization of a prtH-defective mutant of *Porphyromonas gingivalis* W83 is caused by reduced degradation of complement-derived opsonins. J Immunol 154: 5331–5337, 1995.

56. Kesavalu L, Holt S C, Ebersole J L. Trypsin-like protease activity of *Porphyromonas gingivalis* as a potential virulence factor in a murine lesion model. Mibrob Pathog 20: 1–10, 1996.

57. Robert F A, Richardson G J, Michalek S M. Effects of *Porphyromonas gingivalis* and *Escherichia coli* liposaccharides on mononuclear phagocytes. Infect Immunity 65: 3248–3254, 1997.

58. Morrison D C, Ryan J L. Endotoxins and disease mechanisms. Annu Rev Med 38: 417–432, 1987.

59. Agarwal S, Piesco N P, Johns L P, Riccelli A E. Different expression of IL-1β, TNFα, IL-6 and IL-8 in human monocytes in response to lipopolysaccharides from different microbes. J Dent Res 74: 1057–1065, 1995.
60. Reife R A, Shapiro R A, Bamber B A, Berry K K, Mich G E, Darveau R P. *Porphyromonas gingivalis* lipopolysaccharide is poorly recognized by molecular components of innate host defense in a mouse model of early inflammation. Infect Immunity 63: 4686–4694, 1995.
61. Saito A, Sojar H T, Genco R J. *Porphyromonas gingivalis* surface components induce interleukin-1 release and tyrosine phosphorylation in macrophages. FEMS Immunol Med Mibrobiol 15: 51–57, 1996.
62. Reddi K, Wilson M, Nair S, Poole S, Henderson B. Comparison of the pro-inflammatory cytokine stimulating activity of the surface associated proteins of periodontopathic bacteria. J Periodont Res 31: 120–130, 1996.
63. Tokoro Y, Yamamoto T, Hara K. IL-1β mRNA as the predominant inflammatory cytokine transcript: Correlation with inflammatory cell infiltration into human gingiva. J Oral Pathol Med 25: 225–231, 1996.
64. Dinarello Calif., Thompson R C. Blocking IL-1: interleukin 1 receptor antagonist in vivo and in vitro. Immunol Today 12: 404–410, 1991.
65. Change D M. Cellular signals for the induction of human interleukin-1 receptor antagonist. Clin Immunol Immunopathol 74: 23–30, 1995.
66. Kline J N, Fisher P A, Monick M M, Hunninghake G W. Regulation of interleukin-1 receptor antagonist by Th1 and Th2 cytokines. Am J Physiol 269: L92–98, 1995.
67. Tilig H, Trehu E, Atkins M D, Dinarello C A, Mier J W. Interleukin-6 as an anti-inflammatory cytokine: induction of circulating IL-1 receptor antagonist and soluble tumor necrosis factor receptor p55. Blood 83: 113–118, 1994.
68. Marsh C D, Pope H A, Wewers M D. Fc gamma receptor crosslinking down regulates IL-1 receptor antagonist and induces IL-1 beta in mononuclear phagocytes stimulated with endotoxin or *Staphylococcus aureus*. J Immunol 152: 4604–4611, 1994.
69. Propst A, Propst T, Herold M, Vogel W, Judmaier G. Interleukin-1 receptor antagonist in differential diagnosis of inflammatory bowel disease. Eur J Gastroenterol Hepatol 7: 1031–1036, 1995.
70. Suzuki H, Takemura H, Kashiwagi H. Interleukin-1 receptor antagonist in patients with active systemic lupus erythematosus. Enhanced production by monocytes and correlation with disease. Arthritis Rheum 38: 1055–1059, 1995.
71. Kjeldsen M, Takemura H, Kashiwagi H. Bacterial-stimulated cytokine production of peripheral mononuclear cells from patients with various periodontitis categories. J Periodontol 66: 139–144, 1995.
72. Wilson M E, Kalmar J R. FcRIIa (CD32): a potential marker defining susceptibility to localized juvenile periodontitis. J Periodontol. 67: 323–331, 1996.
73. Kobayashi T, Westerdaal N AC, Miyazaki A, van der Pol W L, Suzuki T, Yoshie H, van de Winkel J G J, Hara K. Relevance of Immunoglobulin G Fc receptor polymorphism to recurrence of adult periodontitis in Japanese patients. Infection and Immunity 65: 3556–3560, 1997.
74. Kornman K S, Crane A, Wang H Y, di Giovine F S, Newman M G, Pirk F W, Wilson T G, Higginbottom F L, Duff G W. The interleukin-1 genotype as a severity factor in adult periodontal disease. J. Clin. Periodontol. 24: 72–77, 1997.
75. Poland, G A. Ecogenetics '98 Variability in Immune Response to Pathogens: Using measles vaccine to probe immunogenetic determinants of response. Am. J. Hum. Genet. 62: 215–220, 1998.
76. Tiwari J L, Terasaki P I. HLA and Disease Associations, Springer-Verlag, 1985.
77. Cogen R B, J M Roseman, W Al-Joburi, W C Louv, R T Acton, B O Barger, R C P Go, and R A Rasmussen. Host Factors in Juvenile Periodontitis. J Dental Research, 394–399.
78. Nakagawa M, H Kurihara, F Nishimura, O Isoshima, H Arai, K Sawada, A Nagai, Y Murayama. Immunological, genetic, and microbiological study of family members manifesting early-onset periodontitis. J Periodontol 67 (3); 254–63, 1996.
79. Arai H, T Chihara T, K Takahashi, I Akutsu, S Takashiba, F Nishimura, H Kurihara, Y Murayama. Host defensive functions in a family manifesting early-onset periodontitis. J Periodontol 67(4):433–42, 1996.
80. Cebeci I, A Kantarci, E Firatli, S Aygun, H Tanyeri, A K Aydin, M Carin, U Guc, O Tuncer. Evaluation of the frequency of HLA determinants in patients with gingival overgrowth induced by cyclosporine-A. J Clin Periodontol 23:737–42, 1996.
81. Margiotta V, I Pizzo, G Pizzo, A Barbaro. Cyclosporin- and nifedipine-induced gingival overgrowth in renal transplant patients: correlations with periodontal and pharmacological parameters, and HLA-antigens. J Oral Pathol & Med 25: 128–34, 1996.
82. Wilson M E, Kalmar J R. FcγRIIa (CD32): a potential marker defining susceptibility to localized juvenile periodontitis. J Periodontol. 67: 323–331, 1996.
83. Kobayashi T, Westerdaal N AC, Miyazaki A, van der Pol W L, Suzuki T, Yoshie H, van de Winkel J G J, Hara K. Relevance of Immunoglobulin G Fc receptor polymorphism to recurrence of adult periodontitis in Japanese patients. Infection and Immunity 65: 3556–3560, 1997.
84. Human Molec. Gen., 3:801, 1994.
85. Proc. Natl. Acad. of Sci., USA, 85:4397, 1988.
86. Nucleic Acids Research, 22:880, 1994.
87. Proc. Natl. Acad. of Sci., USA, 74:560,1977.
88. Proc. Natl. Acad. of Sci., USA, 74:5463, 1977.
89. Chomocyznksi et al., 1987, Anal. Biochem., 162:156.
90. Zyke et al., 1988, Science, 239:487.
91. Clynes R, Ravetch J V. Cytotoxic antibodies trigger inflammation through Fc receptors. Immunity 3:21–26, 1995.
92. Hazenbos W L, Gessner J E, Hofhuis F M, Kuipers H, Meyer D, Heijnen I A, Schmidt R E, Sandor M, Capel P J, Daeron M, van de Winkel J G, Verbeek J S. Impaired IgG-dependent anaphylaxis and Arthus reaction in FcγRIII (CD16) deficient mice. Immunity 5:181–188, 1996.
93. Clynes R, Dumitru C, Ravetch J V. Uncoupling of immune complex formation and kidney damage in autoimmune glomerulonephritis. Science 279:1052–1055, 1998.
94. Beaulieu A D, Paquin R, Rathanaswami P, McColl S R. Nuclear signaling in human neutrophils. Stimulation of RNA synthesis is a response to a limited number of pro-inflammatory agonists. J Biol Chem 267: 426–432, 1992.
95. Bazzoni R, Cassatella M A, Rossi F, Ceska M, Dewald B, Baggiolini M. Phagocytosing neutrophils produce and release high amounts of the neutrophil activating peptide 1/interleukin 8. J Exp Med 173: 771–774, 1991.

96. Cassatella M A. *Cytokines produced by polymorphonuclear neutrophils: Molecular and biological aspects.* R.G. Landes Co, Austin, Tex. 1996.
97. Pfefferkorn L C, Yeaman G R. Association of IgA-Fc receptors (Fc alpha R) with Fc epsilon RI gamma 2 subunits in U937 cells. Aggregation induces the tyrosine phosphorylation of gamma 2. J Immunol 153:3228–3236, 1994.
98. Haleem-Smith H, Chang E Y, Szallasi Z, Blumberg P M, Rivera J. Tyrosine phosphorylation of protein kinase C-delta in response to the activation of the high-affinity receptor for immunoglobulin E modifies its substrate recognition. Proc Natl Acad Sci USA 92:9112–9116, 1995.
99. Durden D L, Rosen H, Cooper J A. Serine/threonine phosphorylation of the gamma-subunit after activation of the high-affinity Fc receptor for immunoglobulin G. Biochem J 299:569–577, 1994.
100. Lowry M B, Duchemin A-M, Robinson J M, Anderson C L. Functional separation of pseudopod extension and particle internalization during Fc receptor-mediated phagocytosis. J Exp Med 187:161–176, 1998.
101. Quilliam A L, Osman N, McKenzie IF, Hogarth P M. Biochemical characterization of murine Fc gamma RI. Immunology 78:358–363,1993.
102. Indik Z, Chien P, Levinson A I, Schreiber A D: Calcium signaling by the high affinity macrophage Fcγ receptor requires the cytosolic domain. Immunobiol 185: 183, 1992.
103. Kruskal B A, Sastry K, Warner A B, Mathieu C E, Ezekowitz R A B: Phagocytic chimeric receptors require both transmembrane and cytoplasmic domains from the mannose receptor. J Exp Med 176: 1673, 1992.
104. Socolovsky M, Hockaday A R, Allen J M: Human high-affinity Fc IgG receptor (Fc gamma RI)-mediated phagocytosis and pinocytosis in COS cells. Eur J Cell Biol 64:29–44 1994.
105. Ohta Y, Stossel T P, Hartwig J H: Ligand-sensitive binding of acting-binding protein to immunoglobulin G Fc receptor I (FcgRI). Cell 67: 275, 1991.
106. Prins J-B, Todd J A, Rodrigues N R, Ghosh S, Hogarth P M, Wicker L S, Gaffney E, Podolin P L, Fischer P A, Sirotina A, Peterson L B: Linkage on chromosome 3 of autoimmune diabetes and defective Fc receptor for IgG in NOD mice. Science 260: 695, 1993.
107. Paolini R, Renard V, Vivier E, Ochiai K, Jouvin M H, Malissen B, Kinet J-P: Different roles for the FcεRIγ chain as a function of the receptor context. J Exp Med 181: 247, 1995.
108. Lin S, Cicala C, Scharenberg A M, Kinet J-P: The FcεRIβ subunit functions as an amplifier of FCεRIγ-mediated cell activation signals. Cell 85: 985–995, 1996.
109. Jouvin M-H, Adamczewski M, Numerof R, Letourneur O, Valle A, Kinet J-P: Differential control of the tyrosine kinases Lyn and Syk by the two signaling chains of the high affinity immunoglobulin E receptor. J Biol Chem 269: 5918–5925, 1994.
110. Germano P, Gomez J, Kazanietz M G, Blumberg P M, Rivera J: Phosphorylation of the γ chain of the high affinity receptor for immunoglobulin E by receptor-associated protein kinase C-δ. J Biol Chem 269: 23102, 1994.
111. Hou X, Dietrich J, Geisler N OC. The cytoplasmic tail of FcgammaRIIIAalpha is involved in signaling by the low affinity receptor for immunoglobulin G. J Biol Chem 271:22815–22822, 1996.
112. Morton H C, Schiel A E, Janssen S W, van de Winkel J G. Alternatively spliced forms of the human myeloid Fc alpha receptor (CD89) in neutrophils. Immunogenetics 43:246–247, 1996.
113. Edberg J C, Kimberly R P. Cell-type specific glycoforms of FcγRIIIa (CD16): Differential ligand binding. J Immunol 159: 3849–3857, 1997.
114. Salmon, J E, Millard S, Schacter L A, Arnett F C, Ginzler E M, Gourley M F, Ramsey-Goldman R, Kimberly R P: FcγRIIA alleles are heritable risk factors for lupus nephritis in African-Americans. J Clin Invest 97:1348, 1996.
115. Sanders L A M, van de Winkel J G J, Rijkers G T, Voorhorst-Ogink M M, de Haas M, Capel P J, Zegers B J: Fcγ receptor IIa (CD32) heterogeneity in patients with recurrent bacterial respiratory tract infections. J Infect Dis 170:854,1994.
116. Bredius R G M, Derkx B H F, Fijen C A P, de Wit T P, de Haas M, Weening R S, van de Winkel J G J: Fcγ receptor Ia (CD32) polymorphism in fulminant meningococcal septic shock in children. J Infect Dis 170:848, 1994.
117. Yee A M, Ng S C, Sobel R E, Salmon J E. FcγRIIA polymorphism as a risk factor for invasive pneumococcal infections in systemic lupus erythematosus. Arth Rheum 40:1180–1182, 1997.
118. Fijen C A, Bredius R G, Kuijper E J. Polymorphism of IgG Fc receptors in meningococcal disease. Ann Int Med 119:636, 1993.
119. Selvakumar A, Steffens U, Dupont B. Polymorphism and domain variability of human killer cell inhibitory receptors. Immunol Rev 155:183–196, 1997.
120. Gulle H, Samastag A, Eibl M M, Wolf H M. Physical and functional association of FcαR with protein tyrosine kinase Lyn. Blood 81:383–391, 1998.
121. Johnson S A, Pleiman C M, Pao L, Schneringer J, Hippen K, Cambier J C. Phosphorylated immunoreceptor signaling motifs (ITAMs) exhibit unique abilities to bind and activate Lyn and Syk tyrosine kinases. J Immunol 155:4596–4603, 1995.
122. Odin J A, Edberg J C, Painter C J, Kimberly R P, Unkeless J C. Regulation of phagocytosis and [Ca2+]i flux by distinct regions of an Fc receptor. Science 254: 1785–1788, 1991.
123. Edberg J C, Lin C T, Lau D, Unkeless J C, Kimberly R P. The Ca2+ dependence of human Fc gamma receptor-initiated phagocytosis. J Biol Chem 270:22301–22307, 1995.
124. Melendez A, Floto R A, Gillooly D J, Harnett M M, Allen J M. FcγRI coupling to phospholipase D initiates sphingosine kinase-mediated calcium mobilization and vesicular trafficking. J Biol Chem 273:9393–9402, 1998.
125. Janeway C A, Bottomly K. Signals and signs for lymphocyte responses. Cell 76:275–285, 1994.
126. Edberg J C, Kimberly R P. Modulation of Fcγ and complement receptor function by the glycosyl-phosphatidylinositol-anchored form of FcγRIII. J Immunol 152: 5826–5835, 1994.
127. Monteiro R C, Kubagawa H, Cooper M D. Cellular distribution, regulation, and biochemical nature of an Fcα receptor in human. J Immunol 171:597–613, 1990.
128. Monteiro R C, Hostoffer R W, Cooper M D, Bonner J R, Gartland G L, Kubagawa H. Definition of immunoglobulin A receptors on eosinophils and their enhanced expression in allergic individuals. J Clin Invest 92:1681–1685, 1993.

129. DeCarlo A A, Windsor L J, Bodden M K, Harber G J, Birkedal-Hansen B, Birkedal-Hansen H. Activation and novel processing of matrix metalloproteinases by a thio] proteinase from the oral anaerobe *Porphyromonas gingivalis*. J. Dent. Res. 76: 1260–1270, 1997.

130. Pfefferkorn L C, van de Winkel J G, Swink S L. A novel role for IgG-Fc. Transductional potentiation for human high affinity Fc gamma receptor (FcγRI) signaling. J Biol Chem 270:8164–8171, 1995

131. Patry C, Sibille Y, Lehuen A, Monteiro R C. Identification of Fc alpha receptor (CD89) isoforms generated by alternative splicing that are differentially expressed between blood monocytes and alveolar macrophages. J Immunol 156:4442–4448, 1996.

132. Silvain C, Patry C, Launay P, Lehuen A, Monteiro R C. Altered expression of monocyte IgA Fc receptors is associated with defective endocytosis in patients with alcoholic cirrhosis. Potential role for IFNγ. J Immunol 155:1606–1618,1995.

133. Takashiba S, Shapira L, Amar S, Van Dyke T E. Cloning and characterization of the human TNF alpha promoter region. Gene 131: 307–308, 1993.

134. Furutani Y, Notake M, Fukui T, Ohue M, Nomura H, Yamada M, Nakamura S. Complete nucleotide sequence of the gene for human interleukin 1 alpha. Nucleic Acids Res 14: 3167–3179, 1986.

135. Gray J G, Chandra G, Clay W C, Stinnett S W, Haneline S A, Lorenz J J, Patel I R, Wisely G B, Furdon P J, Taylor J D. A CRE/ATF-like site in the upstream regulatory sequence of the human interleukin 1 beta gene is necessary for induction in U937 and THP-1 monocytic cell lines. Mol Cell Biol 13: 6678–6689, 1993.

136. Jenkins J K, Drong R F, Shuck M E, Bienkowski M J, Slightom J L, Arend W P, Smith M F Jr. Intracellular IL-1 receptor antagonist promoter: cell type-specific and inducible regulatory regions. J Immunol 158: 748–755, 1997.

137. Yasukawa K, Hirano T, Watanabe Y, Muratani K, Matsuda T, Nakai S, Kishimoto T. Structure and expression of human B cell stimulatory factor-2 (BSF-2/IL-6) gene. EMBO Journal 6: 2939–2945, 1987.

138. Kube D, Platzer C, von Knethen A, Straub H, Bohlen H, Hafner M, Tesch H. Isolation of the human interleukin 10 promoter. Characterization of the promoter activity in Burkitt's lymphoma cell lines. Cytokine 7: 1–7, 1995.

139. Eskdale J, Kube D, Tesch H, Gallagher G. Mapping of the human IL10 gene and further characterization of the 5' flanking sequence. Immunogenetics 46: 120–128, 1997.

140. Coligan J E, Kruisbeek A M, Margulies D H, Shevatch E M, Strober W. *Current Protocols in Immunology*, John Wiley and Sons, 1998.

141. Russell M W, Mansa B. Complement-fixing properties of human IgA antibodies: alternative pathway complement activation by plastic-bound, but not by specific antigen-bound IgA. Scand. J. Immunol. 30: 175–183, 1989.

142. Mestecky J, Kilian M. Immunoglobulin A (IgA). Methods Enzymol. 116: 37–75, 1985.

143. Russell M W, Brown T A, Radl J, Haaijman J J, Mestecky J. Assay of human IgA subclass antibodies in serum and secretions by means of monoclonal antibodies. J. Immunol. Methods 87:87–93, 1986.

144. Edberg J C, Barinsky M, Redecha P B, Salmon J E, Kimberly R P. FcγRIII expressed on cultured monocytes is a N-glycosylated transmembrane protein distinct from FcγRIII expressed on natural killer cells. J Immunol 144:4729–4734, 1990.

145. Sengupta T K, Chen A, Zhong Z, Damell J E, Jr., Ivashkiv L B. Activation of monocyte effector genes and STAT family transcription factors by inflammatory synovial fluid is independent of interferon gamma. J Exp Med 181:1015–1025, 1995.

146. Kita H, Abu-Ghazaleh RI, Sur S, Gleich G J. Eosinophil major basic protein induces degranulation and IL-8 production by human eosinophils. J. Immunol. 154: 4749–4758 (1995).

147. Pricop L, Salmon J E, Edberg J C, Beavis A J. Flow cytometric quantitation of attachment and phagocytosis in phenotypically defined subpopulations of cells using PKH26-labeled FcγR-specific probes. J Immunol Meth 205:55–65, 1997.

148. Edberg J C, Moon J J, Chang D J, Kimberly R P. Differential regulation of human neutrophil FcγRIIa (CD32) and FcγRIIIb (CD16)-induced Ca2+ transients. J Biol Chem 273:8071–8079, 1998.

149. Weisbart R H, Kacena A, Schuh A, Golde D W. GM-CSF induces human neutrophil IgA-mediated phagocytosis by an IgA Fc receptor activation mechanism. Nature 332:647–648, 1988.

150. Giuffrè L, Cordey A-S, Monai N, Tardy Y, Schapira M, Spertini O. Monocyte adhesion to activated aortic endothelium: Role of L-selectin and heparin sulfate proteoglycans. J Cell Biol 136: 945–956, 1997.

151. Scott C B, Ratcliffe D R, Cramer E B. Human monocytes are unable to bind to or phagocytize IgA and IgG immune complexes formed with influenza virus in vitro. J. Immunol. 157:351–359, 1996.

One skilled in the art will readily appreciate that the present invention is well adapted to carry out the objectives and obtain the ends and advantages mentioned, as well as those inherent therein. The present examples along with the methods, procedures, treatments, molecules and specific compounds described herein are presently representative of preferred embodiments, are exemplary and are not intended as limitations on the scope of the invention. Changes therein and other uses will occur to those skilled in the art which are encompassed within the spirit of the invention as defined by the scope of the appended claims.

What is claimed is:

1. A method of correlating an FcαRI induced function of intracellular calcium flux or interleukin-6 release or TNFα release of a cell in a host expressing FcαRI with an FcαRI amino acid sequence, said method comprising:
   identifying said FcαRI genotype of said cell at nucleotide 844 corresponding to an amino acid sequence codon 248 as being glycine;
   quantifying said FcαRI induced function by said cell expressing FcαRI; and
   comparing FcαRI induced function by said cell and FcαRI induced function by a second cell, said second cell expressing a second FcαRI genotype at nucleotide 844 that corresponds to serine at said amino acid sequence codon 248, wherein the FcαRI induced function of intracellular calcium flux or interleukin-6 release or TNFα release of the cell in the host expressing FcαRI correlates with the FcαRI amino acid sequence codon 248.

2. The method of claim 1 wherein said cell is selected from the group consisting of: a neutrophil, a monocyte, a myeloid cell, and a mucus secreting cell.

3. A method for determining FcαRI induced function of increased intracellular calcium flux or greater interleukin-6 release or less TNFα release specific to an individual human, said method comprising: genotyping DNA encoding FcαRI for nucleotide 844 corresponding to a codon identity at codon 248 as being glycine, said DNA being obtained from said individual human, wherein the FcαRI induced function specific to said individual human is relative to codon 248 being serine.

4. The method of claim 3 wherein genotyping utilizes PCR typing with a sequence specific primer for a polymorphic exon.

5. The method of claim 4 wherein said primer is selected from the group consisting of SEQ ID No. 1, SEQ ID No. 2, SEQ ID No. 3, or SEQ ID No. 4.

6. A method of prognosticating a human CD89 expressing cellular response, said method comprising:
   establishing a correlation between a FcαRI genotype at nucleotide 844 as to A and a cellular response selected from the group consisting of: increased intracellular calcium flux, greater interleukin-6 release and less TNFα release relative to nucleotide 844 being G;
   genotyping a patient for FcαRI to yield a patient FcαRI genotype at nucleotide 844;
   comparing said FcαRI genotype with said patient genotype; and
   determining said cellular response based on said patient genotype, wherein the human CD89 expressing cellular response is prognosticated based on the nucleotide 844 genotype being A and the cellular response is selected from the group consisting of: increased intracellular calcium flux, greater interleukin-6 release and less TNFα release.

7. The method of claim 6 wherein genotyping utilizes PCR typing with a sequence specific primer for a polymorphic exon.

8. The method of claim 7 wherein said primer is selected from the group consisting of those shown in SEQ ID Nos. 1, 2, 3 and 4.

9. The method of claim 6 wherein genotyping comprises purifying FcαRI expressing cells from said patient; extracting nucleic acids from said cells; and determining whether the nucleic acid encodes a predetermined polymorphic FcαRI nucleic acid sequence.

10. The method of claim 9 wherein the nucleic acid is selected from the group consisting of: RNA and DNA.

* * * * *